US006458559B1

(12) United States Patent
Shi et al.

(10) Patent No.: US 6,458,559 B1
(45) Date of Patent: Oct. 1, 2002

(54) MULTIVALENT RNA APTAMERS AND THEIR EXPRESSION IN MULTICELLULAR ORGANISMS

(75) Inventors: Hua Shi; John T. Lis, both of Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/296,328

(22) Filed: Apr. 22, 1999

Related U.S. Application Data

(60) Provisional application No. 60/082,652, filed on Apr. 22, 1998.

(51) Int. Cl.$^7$ ......................... C12N 15/63; C12N 15/11; C12N 5/16

(52) U.S. Cl. ................... 435/69.1; 435/348; 435/320.1; 536/23.1; 536/24.1

(58) Field of Search ........................... 800/8; 435/91.21, 435/6, 172.1, 69.1, 348, 320.1; 536/23.1, 24.1

(56) References Cited

U.S. PATENT DOCUMENTS

| | | |
|---|---|---|
| 5,270,163 A | 12/1993 | Gold et al. |
| 5,473,060 A | 12/1995 | Gryaznov et al. |
| 5,571,903 A | 11/1996 | Gryaznov |
| 5,582,981 A | 12/1996 | Toole et al. |
| 5,593,835 A | 1/1997 | Rando et al. |
| 5,594,121 A | 1/1997 | Froehler et al. |
| 5,614,503 A | 3/1997 | Chaudhary et al. |
| 5,631,146 A | 5/1997 | Szostak et al. |
| 5,639,595 A | 6/1997 | Mirabelli et al. |
| 5,643,890 A | 7/1997 | Iversen et al. |
| 5,645,985 A | 7/1997 | Froehler et al. |
| 5,656,739 A * | 8/1997 | Cubicciotti ................ 536/23.1 |
| 5,658,738 A | 8/1997 | Nadeau et al. |
| 5,681,702 A | 10/1997 | Collins et al. |
| 5,683,987 A | 11/1997 | Smith |
| 5,688,670 A | 11/1997 | Szostak et al. |
| 5,756,291 A | 5/1998 | Griffin et al. |
| 5,792,613 A | 8/1998 | Schmidt et al. |
| 5,840,867 A | 11/1998 | Toole et al. |
| 5,861,501 A | 1/1999 | Benseler et al. |
| 6,010,884 A * | 1/2000 | Griffiths ................ 435/69.7 |

FOREIGN PATENT DOCUMENTS

| | | |
|---|---|---|
| EP | 0 710 668 A2 | 5/1996 |
| EP | 0 775 745 A2 | 5/1997 |
| EP | 0 784 984 A2 | 7/1997 |
| WO | WO 94/06811 | 3/1994 |
| WO | WO 95/11910 | 5/1995 |
| WO | WO 96/40159 | 12/1996 |
| WO | WO 97/20031 | 6/1997 |

OTHER PUBLICATIONS

Chen et al., Multitarget–ribozyme directed to cleave at up to nine highly conserved HIV–1 env RNA regions inhibits HIV–1 replication–potential effectiveness against most presently sequenced HIV–1 isolates, Nucleic Acids Research, vol. 20, No. 17, pp. 4581–4589.*

Ellington, A.D., "RNA Selection. Aptamers Achieve the Desired Recognition," *Curr. Biol.* 4(5):427–429 (1994).

Yamamoto et al., "In vitro Selection of RNA Aptamers That Can Bind Specifically to Tat Protein of HIV–1," *Nucleic Acids Symp. Ser.* 34:145–146 (1995).

Tian et al., "Dissecting Protein:Protein Interactions Between Transcription Factors With an RNA Aptamer," *RNA* 1(3):317–326 (1995).

Burgstaller et al., "Structural Probing and Damage Selection of Citrulline– and Arginine–specific RNA Aptamers Identify Base Proteins Required for Binding," *Nucleic Acids Res.* 23(23):4769–4776 (1995).

Symensma et al., "RNA Aptamers Selected to Bind Human Immunodeficiency Virus Type 1 Rev in vitro are Rev Responsive in vivo," *J. Virol.* 70(1):179–187 (1996).

Conrad et al., "In vitro Selection of Nucleic Acid Aptamers That Bind Proteins, " *Methods Enzymol.* 267:336–337 (1996).

Hale et al., "Protein Synthesis Editing by a DNA Aptamer," *Proc. Natl. Acad. Sci. USA* 93(7):2755–2758 (1996).

Ye et al., "Deep Penetration of an Alpha–helix into a Widened RNA Major Groove in the HIV–1 Rev Peptide–RNA Aptamer Complex," *Nat. Struct. Biol.* 3(12):1026–1033 (1996).

Li et al., "RNA Aptamers for Yeast Ribosomal Protein L32 Have a Conserved Purine–rich Internal Loop," *RNA* 3(3):245–254 (1997).

Moine et al., "The RNA Binding Site of S8 Ribosomal Protein of *Escherichia coli*:Selex and Hydroxyl Radical Probing Studies," *RNA* 3(3):255–268 (1997).

(List continued on next page.)

Primary Examiner—John S. Brusca
(74) Attorney, Agent, or Firm—Nixon Peabody LLP

(57) ABSTRACT

The present invention relates to a monovalent RNA aptamer that binds to Drosophila splicing factor B52 and a multivalent RNA aptamer that includes at least two RNA aptamer sequences linked together. Also disclosed are isolated or constructed DNA molecules which encode either a monovalent RNA aptamer or a multivalent RNA aptamer of the present invention, an engineered gene encoding a multivalent RNA aptamer of the present invention, and host cells and expression systems which contain either a heterologous DNA molecule or a heterologous gene of the present invention. Further aspects of the present invention relate to a method of expressing a multivalent RNA aptamer in a cell, a method of increasing activity of a splicing factor protein in a cell, and a method of inhibiting activity of a target molecule in a cell. A transgenic non-human organism whose somatic and germ cell lines contain an engineered gene encoding a multivalent RNA aptamer is also disclosed.

62 Claims, 21 Drawing Sheets

OTHER PUBLICATIONS

Eaton et al., "Post–SELEX Combinatorial Optimization of Aptamers," *Bioorg. Med. Chem.* 5(6):1087–1096 (1997).

Gilbert et al., "RNA Aptamers That Specifically Bind to a K Ras–derived Farnesylated Peptide," *Bioorg. Med. Chem.* 5(6)1115–1122 (1997).

Marshall et al., "A Biopolymer by Any Other Name Would Bind as Well: A Comparison of the Ligand–binding Pockets Of Nucleic Acids and Proteins," *Structure* 5(6):729–734 (1997).

Klug et al., "In vitro and in vivo Characterization of Novel mRNA Motifs That Bind Special Elongation Factor SelB," *Proc. Natl. Acad. Sci. USA* 94(13)6676–6681 (1997).

Urvil et al., "Selection of RNA Aptamers That Bind Specifically to the NS3 Protease of Hepatitis C Virus," *Eur. J. Biochem.* 248(1)130–138 (1997).

Kumar et al., "Isolation of RNA Aptamers Specific to the NS3 Protein of Hepatitis C Virus From a Pool of Completely Random RNA," *Virology* 237(2):270–282 (1997).

Weiss et al., "RNA Aptamers Specifically Interact With the Prion Protein PrP," *J. Virol.* 71(11):8790–8797 (1997).

Shi et al., "Artificial Genes Expressing RNA Aptamers as Specific Protein Inhibitors in vivo," *Nucleic Acids Symposium Series* 36:194–196 (1997).

Shi et al., "A Specific RNA Hairpin Loop Structure Binds the RNA Recognition Motifs of the Drosophila SR Protein B52," *Mol. Cell. Biol.* 17(5):2649–2657 (1997).

Shi, "Perturbing Protein Function with RNA Aptamers," Thesis, Cornell University, University Microfilms, Inc. (1997).

* cited by examiner

Fig. 2A

Aptamer sequences

BBS#4,14,15.  ucaacugccaucuaggcAGGGUAACGAUCAACCUGGGCGACAGCUGCCCUGCCGUCCAaguacu

BBS#8.  ggagaauucaacugccaucuaggcUGGUCAACCAGGCGACCGCCACCCGCGGCGCCAAUACCU

BBS#11.  cUGCUCACGAGUCCAUGACCAGUACGAUCAACCAGGCGACaguacuacaagcuucuggacucg

BBS#23.  CCAACUGCUAAGAAGCAUCCUGUACGAUCAACCCGGCGACaguacuacaagcuucuggacucg

Constant Flanking Sequence

5'-gggag aauuc aacug ccauc uaggc -(N$_{40}$)- aguac uacaa gcuuc uggac ucggu-3'

Fig. 4

| | RNA | Sequence and Secondary Structure | Energy | Affinity |
|---|---|---|---|---|
| Deletion | BBS-I/Long (SEQ. ID. No. 25) | GGCUGGUCAACCAGGCGACCGCCACCCGCGCGC<br>(((-((((---------))))))))---------- | -13.0 | ++++ |
| | BBS-I (SEQ. ID. No. 26) | GGCUGGUCAACCAGGCGACCGCC<br>(((-((((---------)))))))) | -11.0 | ++++ |
| | BBS-I/NoBulge (SEQ. ID. No. 27) | GGCGGUCAACCAGGCGACCGCC<br>(((((((---------)))))))) | -14.7 | ++++ |
| | BBS-II (SEQ. ID. No. 28) | GGGUACGAUCAACCAGGCGACAGUACCC<br>((((((--((---------))--)))))) | -10.8 | ++++ |
| | bbs-II (SEQ. ID. No. 29) | GGACGAUCAACCAGGCGACAGU<br>--<<--<<--------->>-->> | ? | +++ |
| | AltStem (SEQ. ID. No. 30) | GGUCAACCAGGCGAC<br>-(((-----)))--- | -3.4 | + |
| Substitution | FlipBBS-II (SEQ. ID. No. 31) | GGCAUGAAUCAACCAGGCGACGCAUGCC<br>((((((--((---------))--)))))) | -9.7 | + |
| | TransBBS-I (SEQ. ID. No. 32) | GGAUGUCAACCAGGCGACAUCC<br>(((((((---------)))))))) | -11.3 | + |
| | bbs-II/5'Stem (SEQ. ID. No. 33) | GGACUGUCAACCAGGCGACAGU<br>--((((((---------)))))) | -8.9 | + |
| | bbs-II/3'Stem (SEQ. ID. No. 34) | GGACGGUCAACCAGGCGACCGU<br>--((((((---------)))))) | -10.4 | ++++ |
| Antisense | AntiBBS-I (SEQ. ID. No. 35) | GGCGGUCGCCUGGUUGACCAGCC<br>(((((((((------))))))-))) | -11.4 | – |
| | AntiBBS-II (SEQ. ID. No. 36) | GGACUGUCGCCUGGUUGAUCGU<br>-(((((-----))))------ | -3.5 | – |
| | UUCG/BBS (SEQ. ID. No. 37) | GGUCGCCUGGUUGAUCUUCGGAUCAACCAGGCGACA<br>-(((((((((((((((----))))))))))))))))- | -34.5 | – |

Fig. 7

| Construct Series | Promoters | Transcriptional Templates | Vectors | Utility |
|---|---|---|---|---|
| pT7BBS | T7 | BBS(5.1), BBS(5.2), BBS(5.4), BBS(5.8), BBS(5.12), BBS(5.1-), BBS(5.2-), BBS(5.4-) | pGEM-3Z or pSP73 | *in vitro* transcription |
| pHicBBS | Hic | BBS(5.2), BBS(5.12) | pHic-L | *in vivo* (cells) fast induction |
| pMtnBBS | Mtn | BBS(5.2), BBS(5.12), BBS(5.2-), BBS(5.12-) | pMtnEX | *in vivo* (cells) slow induction |
| pW8-HicBBS | Hic | BBS(5.2), BBS(5.12) | pW8 | *in vivo* (flies) direct induction |
| pUASBBS | UAShs | BBS(5.1), BBS(5.2), BBS(5.12), BBS(5.1-) | pUAST | *in vivo* (flies) indirect induction |

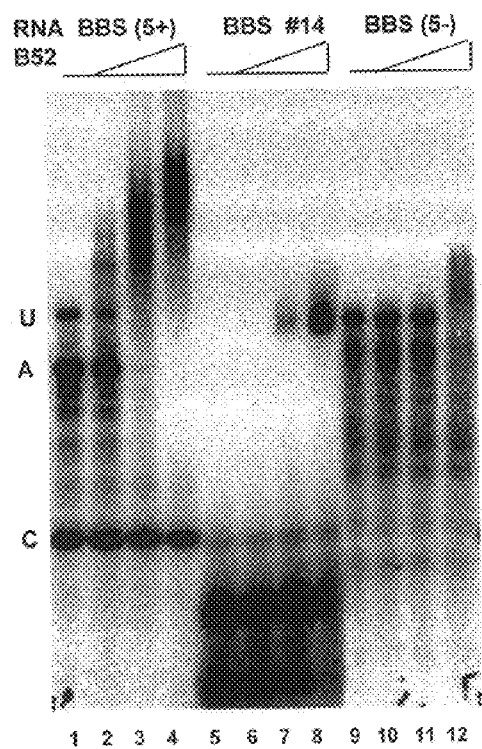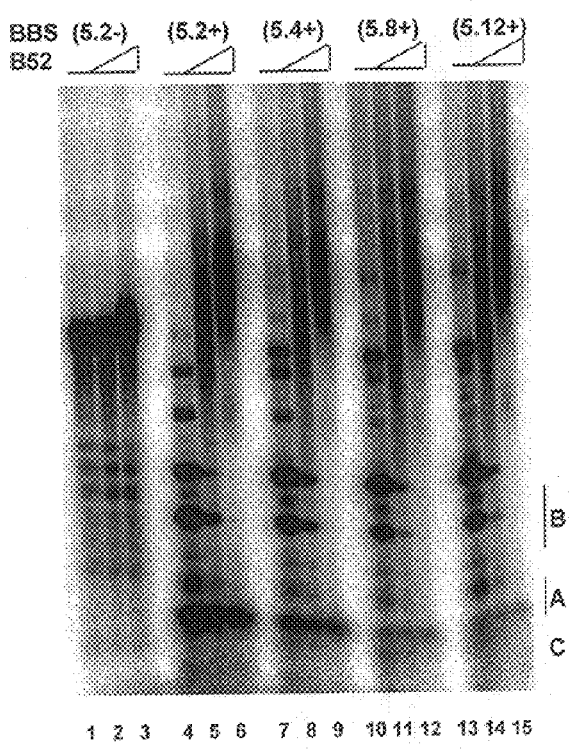
Fig. 9A
Fig. 9B

Fig. 12A
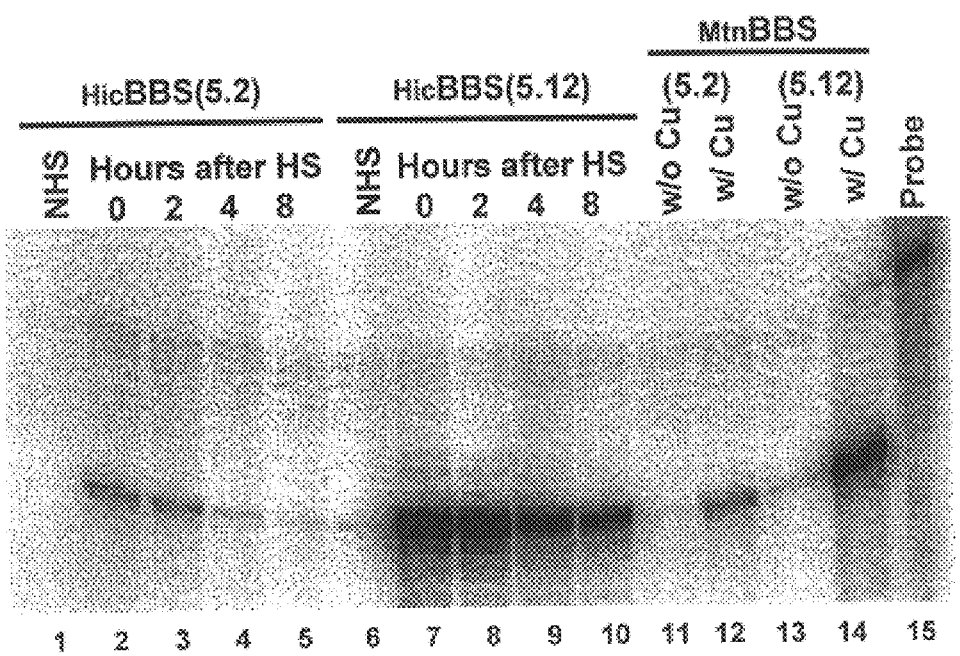
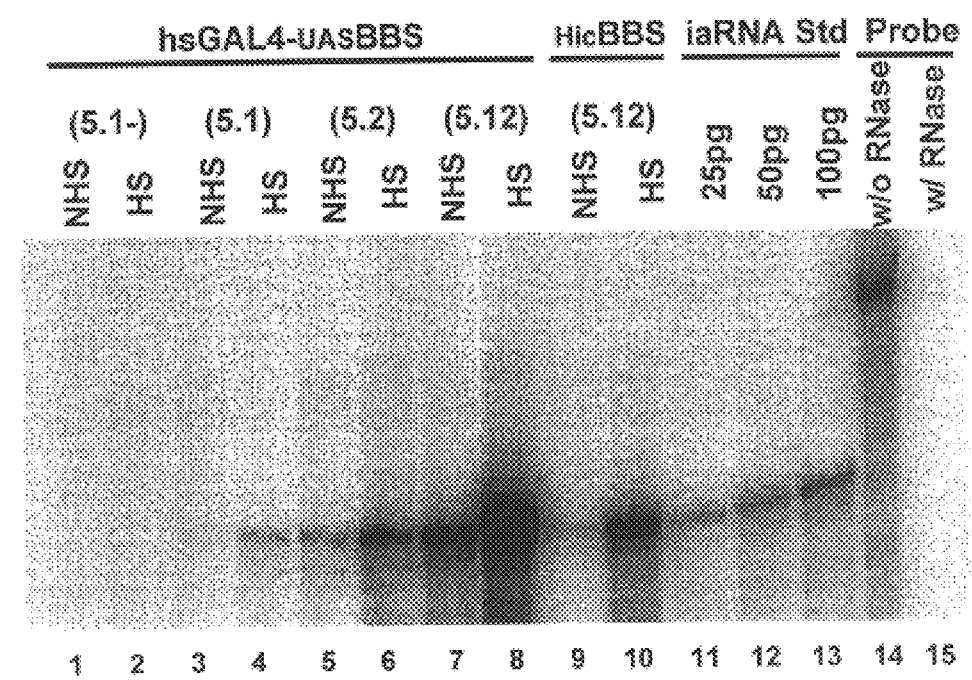
Fig. 12B

Fig. 13A
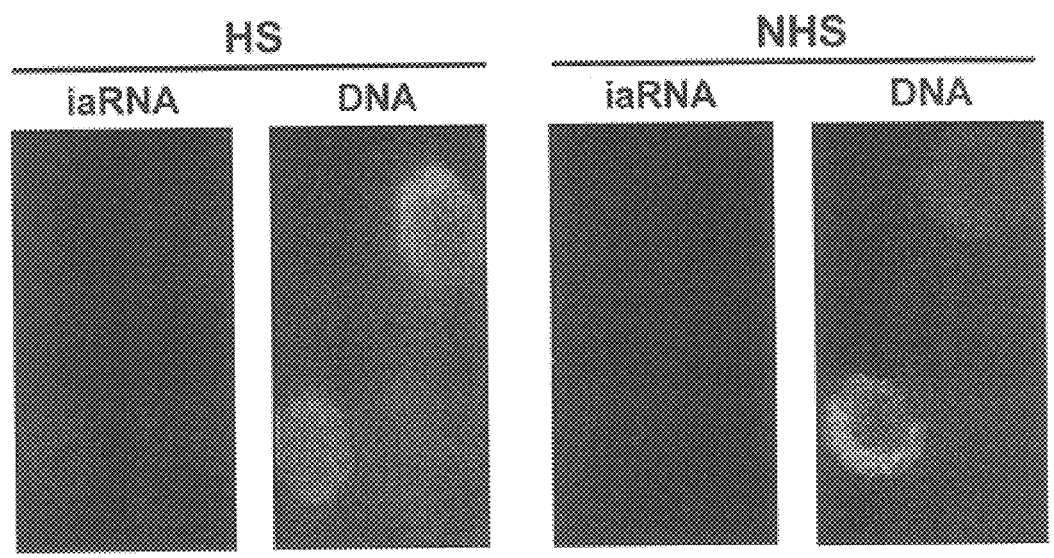
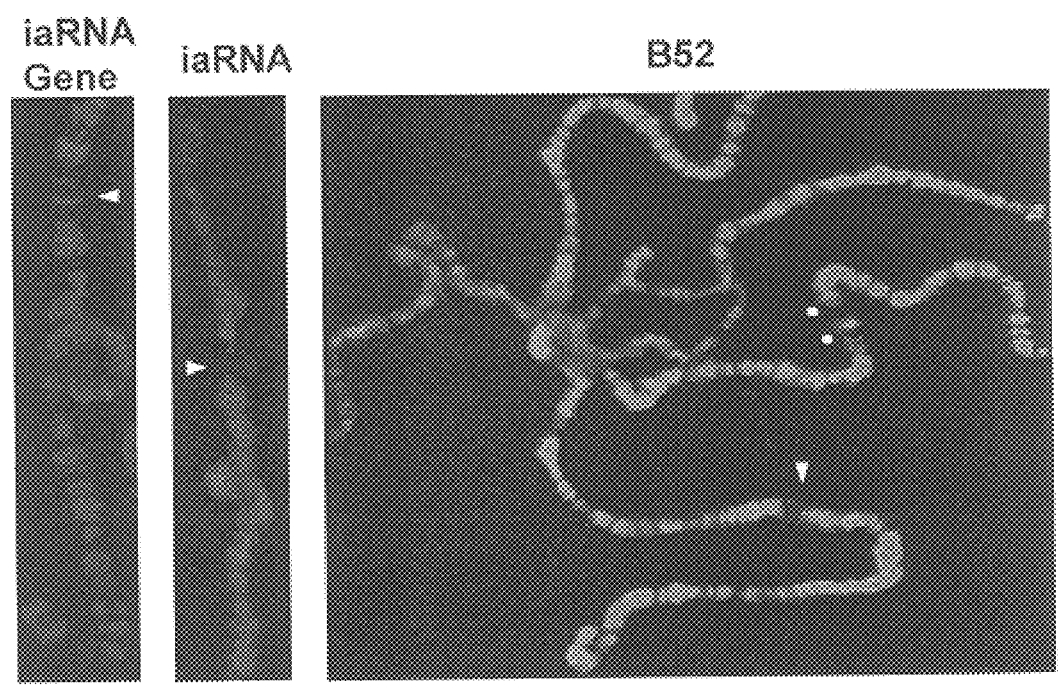
Fig. 13B

Fig. 15A

| Selfing A (Experiment) | Selfing B (Control) |
|---|---|
| $\dfrac{P[w^+,uASBBS(5.12)]}{CyO}$ ; $\dfrac{P[w^+,hsGAL4]}{TM2,Ubx}$ | $\dfrac{P[w^+,uASBBS(5.12)]}{CyO}$ ; $\dfrac{P[w^+,uASBBS(5.12)]}{TM2,Ubx}$ |

Fig. 15B

Viability of the BBS expressing progeny

| Phenotype of progeny | Expected fraction | hsGAL4 copies | UASBBS copies | Expt. 1 A | Expt. 1 B | Viability | Expt. 2 A | Expt. 2 B | viability |
|---|---|---|---|---|---|---|---|---|---|
| w | 1/16 | 2 | 2 | 12 | 22 | 54% | 12 | 23 | 52% |
| w, Ubx | 1/8 | 1 | 2 | 30 | 50 | 60% | 37 | 47 | 78% |
| w, Cy | 1/8 | 2 | 1 | 23 | 51 | 45% | 26 | 66 | 40% |
| w, Cy, Ubx | 1/4 | 1 | 1 | 89 | 100 | 89% | 105 | 98 | 107% |

Fig. 17A $$\frac{P[w^+,GAL4]}{P[w^+,GAL4]} \times \frac{P[w^+,UASBBS(5.12)]}{P[w^+,UASBBS(5.12)]} ; \frac{P[w^+,UASB52]}{P[w^+,UASB52]}$$

↓

{B52 + BBS}

| Phenotype | GAL4 Source | {B52} | {B52 + BBS} | {BBS} |
|---|---|---|---|---|
| Salivary glands | dppGAL4 | 100% undeveloped | 100% developed with near normal morphology | Normal |
| Bristles (7 pairs) | hsGAL4 | Score 0-2 | Score 10-12 | Normal (Score 14) |
| Wings | dppGAL4 | 0% unfolded | 20% unfolded | Normal |
| Abdominal sternites | G-17 | 40% defect | <5% defect | Normal |
| Lethality | I-65 | No survivor beyond 2nd instar | 60% survive to adult | >90% survive to adult |

Fig. 17H

Fig. 17B    Fig. 17C    Fig. 17D
Salivary Glands
{B52}    {B52+BBS}    {BBS}
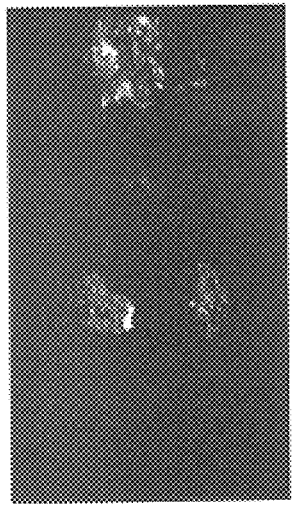  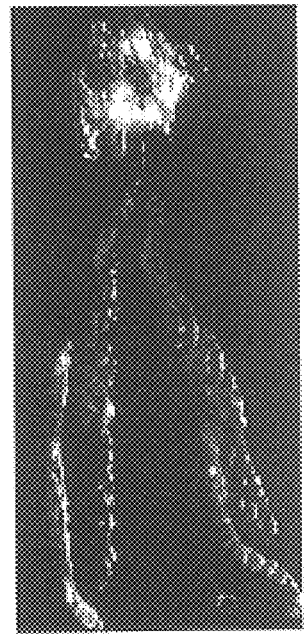
(GAL4 Source: dppGAL4)
Bristles
{B52}    {B52+BBS}    {BBS}
 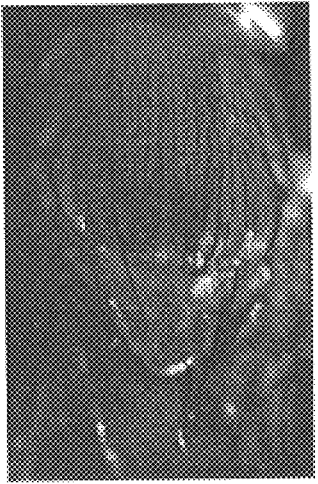 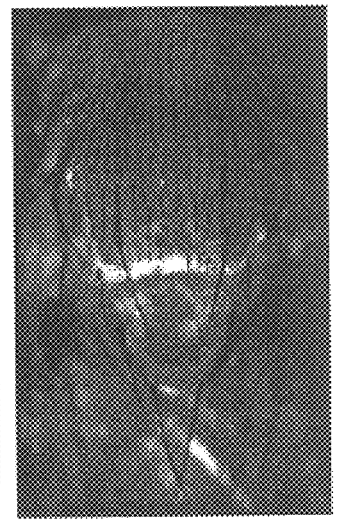
Score: 1    Score: 11    Score: 14
(GAL4 Source: hsGAL4)
Fig. 17E    Fig. 17F    Fig. 17G Fig. 17I
$$\frac{P[w^+, UASBBS]}{P[w^+, UASBBS]} \times \frac{P[w^+, UASB52]}{In(2LR)O, Cy} ; \frac{P[w^+, hsGAL4]}{TM2, Ubx^{130}}$$
↓
{B52 + BBS}
Fig. 17J
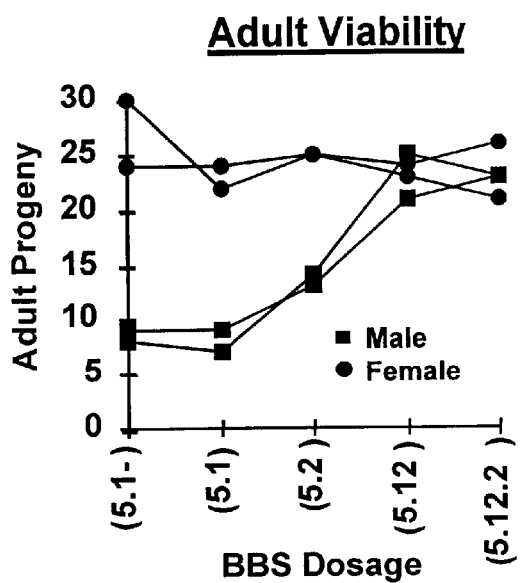
Fig. 17K
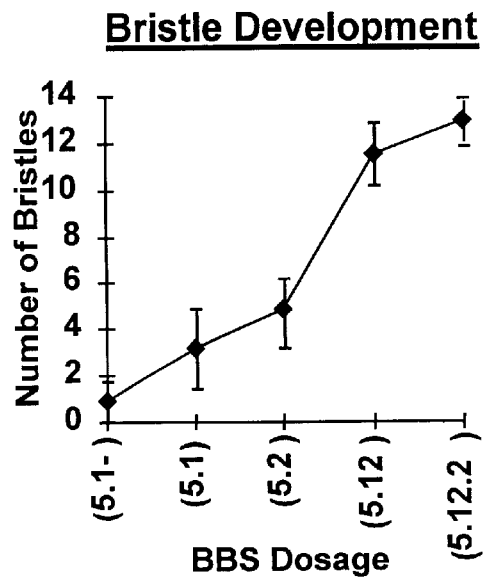

SEQUENCE LISTING

<160> NUMBER OF SEQ ID NOS: 37

<210> SEQ ID NO 1
<211> LENGTH: 90
<212> TYPE: RNA
<213> ORGANISM: Artificial Sequence
<220> FEATURE:
<223> OTHER INFORMATION: Description of Artificial Sequence: monovalent
      RNA aptamer for Drosophila splicing factor B52

<400> SEQUENCE: 1
gggagaauuc aacugccauc uaggcagggu aacgaucaac cuggcgacag cugcccugcc      60
guccaaguac uacaagcuuc uggacucggu                                      90

```
<210> SEQ ID NO 2
<211> LENGTH: 89
<212> TYPE: RNA
<213> ORGANISM: Artificial Sequence
<220> FEATURE:
<223> OTHER INFORMATION: Description of Artificial Sequence: monovalent
      RNA aptamer for Drosophila splicing factor B52

<400> SEQUENCE: 2
gggagaauuc aacugccauc uaggcugguc aaccaggcga ccgccacccg cgcgcgcaau    60
accuaguacu acaagcuucu ggacucggu                                      89

<210> SEQ ID NO 3
<211> LENGTH: 89
<212> TYPE: RNA
<213> ORGANISM: Artificial Sequence
<220> FEATURE:
<223> OTHER INFORMATION: Description of Artificial Sequence: monovalent
      RNA aptamer for Drosophila splicing factor B52

<400> SEQUENCE: 3
cgacaguacu acaagcuucu ggacucggu                                      89

<210> SEQ ID NO 4
<211> LENGTH: 90
<212> TYPE: RNA
<213> ORGANISM: Artificial Sequence
<220> FEATURE:
<223> OTHER INFORMATION: Description of Artificial Sequence: monovalent
      RNA aptamer for Drosophila splicing factor B52

<400> SEQUENCE: 4
gggagaauuc aacugccauc uaggcccaac ugcuaagaag cauccuguac gaucaacccg    60
gcgacaguac uacaagcuuc uggacucggu                                     90

<210> SEQ ID NO 5
<211> LENGTH: 17
<212> TYPE: RNA
<213> ORGANISM: Artificial Sequence
<220> FEATURE:
<223> OTHER INFORMATION: Description of Artificial Sequence: binding
      sequence of RNA aptamers for Drosophila B52
      splicing factor
<221> NAME/KEY: N_region
<222> LOCATION: (2)
<223> OTHER INFORMATION: The n at position 2 can be either a or g
<221> NAME/KEY: N_region
<222> LOCATION: (9)
<223> OTHER INFORMATION: The n at position 9 can be either u, a, or c
<221> NAME/KEY: N_region
<222> LOCATION: (16)
<223> OTHER INFORMATION: The n at position 16 can be either a or c

<400> SEQUENCE: 5
gnucaaccng gcgacng                                                   17

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: 5' DNA
      template

<400> SEQUENCE: 6
gtaatacgac tcactatagg gagaattcaa ctgccatcta ggc                      43
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: 3' DNA
      template

<400> SEQUENCE: 7
agtactacaa gcttctggac tcggt                                          25

<210> SEQ ID NO 8
<211> LENGTH: 214
<212> TYPE: RNA
<213> ORGANISM: Artificial Sequence
<220> FEATURE:
<223> OTHER INFORMATION: Description of Artificial Sequence: pentavalent
      RNA aptamer for Drosophila splicing factor B52

<400> SEQUENCE: 8
gcggccgccu ccgcggccgc cugaugaguc cgugaggacg aaacaugcau gucgagagua     60
cgaucaacca ggcgacagua cucucgacga ucaaccaggc gacaguggcu ggucaaccag    120
gcgaccgcca cugcagggua acggucaacc aggcgaccgu uacccggacg gucaaccagg   180
cgaccguuga cuucggucag ucgagaugca uguc                               214

<210> SEQ ID NO 9
<211> LENGTH: 108
<212> TYPE: DNA
<213> ORGANISM: Artificial Sequence
<220> FEATURE:
<223> OTHER INFORMATION: Description of Artificial Sequence: DNA
      encoding monovalent RNA aptamer

<400> SEQUENCE: 9
gtaatacgac tcactatagg gagaattcaa ctgccatcta ggcagggtaa cgatcaacct    60
ggcgacagct gccctgccgt ccaagtacta caagcttctg gactcggt               108

<210> SEQ ID NO 10
<211> LENGTH: 107
<212> TYPE: DNA
<213> ORGANISM: Artificial Sequence
<220> FEATURE:
<223> OTHER INFORMATION: Description of Artificial Sequence: DNA
      encoding monovalent RNA aptamer

<400> SEQUENCE: 10
gtaatacgac tcactatagg gagaattcaa ctgccatcta ggctggtcaa ccaggcgacc    60
gccacccgcg cgcgcaatac ctagtactac aagcttctgg actcggt                107

<210> SEQ ID NO 11
<211> LENGTH: 107
<212> TYPE: DNA
<213> ORGANISM: Artificial Sequence
<220> FEATURE:
<223> OTHER INFORMATION: Description of Artificial Sequence: DNA
      encoding monovalent RNA aptamer

<400> SEQUENCE: 11
gtaatacgac tcactatagg gagaattcaa ctgccatcta ggctgctcac gagtccatga    60
ccagtacgat caaccaggcg acagtactac aagcttctgg actcggt                107

<210> SEQ ID NO 12

<210> SEQ ID NO 12
<211> LENGTH: 108
<212> TYPE: DNA
<213> ORGANISM: Artificial Sequence
<220> FEATURE:
<223> OTHER INFORMATION: Description of Artificial Sequence: DNA
    encoding monovalent RNA aptamer

<400> SEQUENCE: 12

```
gtaatacgac tcactatagg gagaattcaa ctgccatcta ggcccaactg ctaagaagca     60
tcctgtacga tcaacccggc gacagtacta caagcttctg gactcggt                108
```

<210> SEQ ID NO 13
<211> LENGTH: 214
<212> TYPE: DNA
<213> ORGANISM: Artificial Sequence
<220> FEATURE:
<223> OTHER INFORMATION: Description of Artificial Sequence: DNA
    encoding immature RNA transcript

<400> SEQUENCE: 13

```
gtcgagagta cgatcaacca ggcgacagta ctctcgacga tcaaccaggc gacagtggct     60
ggtcaaccag gcgaccgcca ctgcagggta acggtcaacc aggcgaccgt tacccggacg    120
gtcaaccagg cgaccgttga cttcggtcag tcgagatgca tgtcgcggcc gcctccgcgg    180
ccgcctgatg agtccgtgag gacgaaacat gcat                                 214
```

<210> SEQ ID NO 14
<211> LENGTH: 214
<212> TYPE: RNA
<213> ORGANISM: Artificial Sequence
<220> FEATURE:
<223> OTHER INFORMATION: Description of Artificial Sequence: Immature
    RNA transcript

<400> SEQUENCE: 14

```
gucgagagua cgaucaacca ggcgacagua cucucgacga ucaaccaggc gacaguggcu     60
ggucaaccag gcgaccgcca cugcagggua acggucaacc aggcgaccgu uacccggacg    120
gucaaccagg cgaccguuga cuucggucag ucgagaugca ugucgcggcc gccuccgcgg    180
ccgccugaug aguccgugag gacgaaacau gcau                                 214
```

<210> SEQ ID NO 15
<211> LENGTH: 108
<212> TYPE: DNA
<213> ORGANISM: Artificial Sequence
<220> FEATURE:
<223> OTHER INFORMATION: Description of Artificial Sequence: DNA
    template
<221> NAME/KEY: N_region
<222> LOCATION: (26)..(65)
<223> OTHER INFORMATION: The n at any position can be either a, g, c or
    t

<400> SEQUENCE: 15

```
accgagtcca gaagcttgta gtactnnnnn nnnnnnnnnn nnnnnnnnnn nnnnnnnnnn     60
nnnnngccta gatggcagtt gaattctccc tatagtgagt cgtattac                 108
```

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: DNA primer

<400> SEQUENCE: 16

```
gtaatacgac tcactatagg gagaattcaa ctgccatcta                           40
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: DNA primer

<400> SEQUENCE: 17

```
accgagtcca gaagcttgta gt                                             22
```

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: DNA primer

<400> SEQUENCE: 18

```
accgctcgag agtacgatca accaggcgac agtactctcg acgatcaacc aggcgacagt    60
```

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: DNA primer

<400> SEQUENCE: 19

```
aaactgcagt ggcggtcgcc tggttgacca gccactgtcg cctggttgat cgtcgagagt    60
```

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: DNA primer

<400> SEQUENCE: 20

```
aaactgcagg gtaacggtca accaggcgac cgttacccgg acggtcaacc aggcg         55
```

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: DNA primer

<400> SEQUENCE: 21

```
acgcgtcgac tgaccgaagt caacggtcgc ctggttgacc gtccgggtaa cggtc         55
```

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: DNA primer

<400> SEQUENCE: 22

```
accgctcgag atgcatgtcg cggccgcctc cgcggccgcc tgatgagtcc               50
```

<210> SEQ ID NO 23
<211> LENGTH: 50
<212> TYPE: DNA

```
<213> ORGANISM: Artificial Sequence
<220> FEATURE:
<223> OTHER INFORMATION: Description of Artificial Sequence:  DNA primer

<400> SEQUENCE: 23
acgcgtcgac atgcatgttt cgtcctcacg gactcatcag gcggccgcgg            50

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:  Random
      sequence for competitive binding

<400> SEQUENCE: 24
gagacccacc gacacctcgg ccggcggggc ttttagcgag                       40

<210> SEQ ID NO 25
<211> LENGTH: 33
<212> TYPE: RNA
<213> ORGANISM: Artificial Sequence
<220> FEATURE:
<223> OTHER INFORMATION: Description of Artificial Sequence:  Deletion
      variant of monovalent RNA aptamer

<400> SEQUENCE: 25
ggcuggucaa ccaggcgacc gccacccgcg cgc                              33

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence:  Deletion
      variant of monovalent RNA aptamer

<400> SEQUENCE: 26
ggcuggucaa ccaggcgacc gcc                                         23

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence:  Deletion
      variant of monovalent RNA aptamer

<400> SEQUENCE: 27
ggcggucaac caggcgaccg cc                                          22

<210> SEQ ID NO 28
<211> LENGTH: 28
<212> TYPE: RNA
<213> ORGANISM: Artificial Sequence
<220> FEATURE:
<223> OTHER INFORMATION: Description of Artificial Sequence:  Deletion
      variant of monovalent RNA aptamer

<400> SEQUENCE: 28
ggguacgauc aaccaggcga caguaccc                                    28

<210> SEQ ID NO 29
<211> LENGTH: 22
<212> TYPE: RNA
<213> ORGANISM: Artificial Sequence
<220> FEATURE:
```

```
<223> OTHER INFORMATION: Description of Artificial Sequence: Deletion
      variant of monovalent RNA aptamer

<400> SEQUENCE: 29
ggacgaucaa ccaggcgaca gu                                              22

<210> SEQ ID NO 30
<211> LENGTH: 15
<212> TYPE: RNA
<213> ORGANISM: Artificial Sequence
<220> FEATURE:
<223> OTHER INFORMATION: Description of Artificial Sequence: Deletion
      variant of monovalent RNA aptamer

<400> SEQUENCE: 30
ggucaaccag gcgac                                                      15

<210> SEQ ID NO 31
<211> LENGTH: 28
<212> TYPE: RNA
<213> ORGANISM: Artificial Sequence
<220> FEATURE:
<223> OTHER INFORMATION: Description of Artificial Sequence:
      Substitution variant of monovalent RNA aptamer

<400> SEQUENCE: 31
ggcaugaauc aaccaggcga cgcaugcc                                        28

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence:
      Substitution variant of monovalent RNA aptamer

<400> SEQUENCE: 32
ggaugucaac caggcgacau cc                                              22

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence:
      Substitution variant of monovalent RNA aptamer

<400> SEQUENCE: 33
ggacugucaa ccaggcgaca gu                                              22

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence:
      Substitution variant of monovalent RNA aptamer

<400> SEQUENCE: 34
ggacggucaa ccaggcgacc gu                                              22

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Antisense
```

```
                    -continued sequence of monovalent RNA aptamer

<400> SEQUENCE: 35
ggcggucgcc ugguugacca gcc                                          23

<210> SEQ ID NO 36
<211> LENGTH: 22
<212> TYPE: RNA
<213> ORGANISM: Artificial Sequence
<220> FEATURE:
<223> OTHER INFORMATION: Description of Artificial Sequence:  Antisense
      sequence of monovalent RNA aptamer

<400> SEQUENCE: 36
ggacugucgc cugguugauc gu                                           22

<210> SEQ ID NO 37
<211> LENGTH: 36
<212> TYPE: RNA
<213> ORGANISM: Artificial Sequence
<220> FEATURE:
<223> OTHER INFORMATION: Description of Artificial Sequence:  RNA duplex
      containing binding sequence of RNA aptamer for
      Drosophila B52 splicing factor and antisense
      sequence

<400> SEQUENCE: 37
ggucgccugg uugaucuucg gaucaaccag gcgaca                            36
```

MULTIVALENT RNA APTAMERS AND THEIR EXPRESSION IN MULTICELLULAR ORGANISMS

This application claims the benefit of U.S. Provisional Patent Application Serial No. 60/082,652, filed Apr. 22, 1998.

This invention was made in part with Government support under U.S. Public Health Service Grant GM40918 and U.S.D.A. Hatch Project Grant NY(c)-181413. The Government may have certain rights to this invention.

FIELD OF THE INVENTION

The present invention relates to monovalent and multivalent RNA aptamers, constructed DNA molecules and engineered genes which encode the RNA aptamers of the present invention, as well as expression systems, host cells, and transgenic organisms which express the RNA aptamers of the present invention.

BACKGROUND OF THE INVENTION

Cells and organisms are complex adaptive systems in which numerous biological processes are driven by sophisticated macromolecular machinery and regulated by elaborate signal transduction networks, both usually composed of multiple proteins. To better understand and control such processes, new technologies are needed to intervene in protein functions in the real time and space of the living cells. In many cases, such in vivo destructive approaches are needed to expand and extend results obtained from in vitro reconstruction studies. On the other hand, many diseases are known to be caused by either overexpression of certain endogenous genes (such as oncogenes in cancer) or expression of exogenous genes (as in the case of a virus infection), and "anti-gene" therapies are called for to avert or ameliorate the morbidity and mortality caused by these gene products. To inactivate a specific gene or gene product, different techniques are directed at three distinct types of targets: DNA, RNA, and protein. For example, a gene can be altered by homologous recombination, the expression of the genetic code can be blocked at the RNA level by antisense oligonucleotides or ribozymes, and the protein function can be altered or inhibited by antibodies or drugs.

A particularly useful tool resulting from the change of the protein coding function of genes is a conditional allele which displays its mutant phenotype only under certain non-permissive conditions, making it possible to obtain viable cells or organisms when a critical protein is under investigation. More importantly, with a conditional allele it is also possible to target and change specific genes in specific stages of development so that the details of a wrongly assembled protein machine can be identified. Recently there have been many new refinements of this technique. Notably, Struhl and colleagues developed a two-pronged approach to create yeast strains with conditional alleles in which the addition of copper ion leads to the simultaneous cessation of MRNA synthesis and destruction of the target protein in the cell (Moqtaderi et al., "TBP-Associated Factors Are Not Generally Required for Transcriptional Activation in Yeast," *Nature* 383:188–191 (1996)). However, the generation of conditional mutants in higher (i.e., multicellular) eukaryotes is quite difficult. In addition, it is often impossible to assay individual domains or discrete functional surfaces of a protein, since the function of the whole protein is abolished.

Small molecular mass drugs and drug derivatives that directly target proteins have been used not only clinically to rectify disease phenotype, but also in basic research that yielded ample information in mechanistic studies both in vitro and in vivo. These are usually cell-permeable, low molecular weight organic molecules identified from natural sources or designed and synthesized in the laboratory. Usually they are specific ligands of proteins, affecting protein functions upon binding. In many cases they are mimetics of the natural ligands of their targets (or receptors, as they are called in pharmacodynamics). In vivo experiments can be conducted easily with drugs at the cellular level since the administration may be simple diffusion governed by Fick's law. But systemic drug delivery to the organism is usually complicated by many pharmacokinetic factors, making it difficult to institute dosage regimens and assess drug effects at high temporal-resolution. The biggest limitation of using small molecular protein ligands is their availability. It is usually not easy to find such a ligand for a predetermined protein target, either from natural sources or by design. Recently, a general procedure for manipulating protein in vivo at the cellular level was developed, in which a gain of function results from the use of synthetic "dimerizers" derived from an immunosuppressive drug (Ho et al., "Dimeric Ligands Define a Role for Transcriptional Activation Domains in Reinitiation," *Nature* 382:822–826 (1996)). Although this "three-part invention" (Crabtree and Schreiber, "Three-Part Inventions: Intracellular Signaling and Induced Proximity," *TIBS* 21:418–422 1996)) may overcome the difficulty to a certain extent, a ligand-binding domain has to be appended to the target proteins.

As specific protein binding ligands, antibodies can be custom-made for virtually any given protein, due to the clonal selection and maturation function of the immune system. Antibodies raised against specific proteins have made possible many technological advances in the field of molecular biology, including modern immunochemistry (Harlow and Lane, *Antibodies: A Laboratory Manual*, Cold Spring Harbor Laboratory Press, Cold Spring Harbor, N.Y. (1988)). But the in vivo utility of protein reagents like antibodies is severely limited by difficulties in their delivery and their own immunogenicity.

RNA has distinct advantages over proteins and small organic molecules when considering its use to inactivate protein function in vivo. An RNA encoding sequence can be linked to a promoter and this artificial gene introduced into cells or organisms. Depending on the regulatory sequence included, this provides a unique way of constructing a time and/or tissue specific suppresser gene. Such RINA expressing genes are usually smaller than protein-coding genes and can be inserted easily into gene therapy vectors. Unlike a foreign or altered protein, RNA is less likely to evoke an immune response. Antisense molecules and ribozymes have been developed as "code blockers" to inactivate gene function, with their promise of rational drug design and exquisite specificity (Altman, "RNase P in Research and Therapy," *Bio/Technology* 13:327–329 (1995); Matteucci and Wagner, "In Pursuit of Antisense," *Nature* 384 Suppl. (6604):20–22 (1996)). Mechanistically, both antisense oligodeoxynucleotides ("ODNs") and bioengineered ribozymes are expected to achieve specific binding in the first step of their action by forming a stable duplex (or triplex in some cases of the ODNs) with a target nucleotide sequence based on Watson-Crick or Hoogsteen base pairing. However, this mechanism and their ability to disrupt the function of a single gene has never been proven. Furthermore, a wide variety of unexpected non-antisense effects have come to light, especially with the chemically modified compounds. Although some of these side effects may have clinical value, the use of antisense compounds as research reagents is severely limited (Branch, "A Good Antisense Molecule is Hard to Find," *TIBS* 23:45–50 (1998)).

Recently, RNA aptamers have also been explored as research and therapeutic reagents for their ability directly to disrupt protein function. Selection of aptamers in vitro allows rapid isolation of extremely rare RNAs that have high specificity and affinity for specific proteins. Exemplary RNA aptamers are described in U.S. Pat. No. 5,270,163 to Gold et al., Ellington and Szostak, "In vitro Selection of RNA Molecules That Bind Specific Ligands," *Nature* 346:818–822 (1990), and Tuerk and Gold, "Systematic Evolution of Ligands by Exponential Enrichment: RNA Ligands to Bacteriophage T4 DNA Polymerase," *Science* 249:505–510 (1990). Unlike antisense compounds, whose targets are one dimensional lattices, RNA aptamers can bind to the three dimensional surfaces of a protein. Moreover, RNA aptamers can frequently discriminate finely among discrete functional sites of a protein (Gold et al., "Diversity of Oligonucleotide Functions," *Annu. Rev. Biochem.* 64:763–797 (1995)). As research and therapeutic reagents, aptamers not only have the combined advantages of antibodies and small molecular mass drugs, but in vivo production of RNA aptamers also can be controlled genetically. The controlled expression of high affinity RNA aptamers offers a means of rapidly inactivating specific domains of proteins and thereby assessing their function and mechanism of action.

Although gene therapy has the potential for treating many diseases with very low risk of adverse reactions, the efficiency of gene transfer and expression in vivo is still disappointingly low. Assuming that efficient gene transfer can be developed, the next issue would be long-term, stable, or even regulated gene expression at the appropriate level. This is perhaps the greatest shortcoming of present vectors for gene therapy (Anderson, "Human Gene Therapy," *Nature* 392 Suppl. (6679): 25–30 (1998)). Efficient and effective intracellular expression of functional RNA molecules such as aptamers depends on many factors, some of them giving rise to competing and conflicting design requirements. Ideally, the RNA should be productively transcribed, stabilized against rapid degradation, folded correctly, and directed to the subcellular region where its target resides. Genes expressing various inhibitor RNAs have been generated by modifying small RNA transcription units that normally produce tRNAs (Sullenger et al., "Overexpression of TAR Sequences Renders Cells Resistant to Human Immunodeficiency Virus Replication," *Cell* 63:601–608 (1990)), small nuclear RNAs (Noonberg et al., "In vivo Generation of Highly Abundant Sequence-Specific Oligonucleotides for Antisense and Triplex Gene Regulation," *Nucleic Acids Res.* 22:2830–2836 (1994)), or small viral RNAs (Lieber and Strauss, "Selection of Efficient Cleavage Sites in Target RNAs by Using a Ribozyme Expression Library," *Mol. Cell. Biol.* 15:540–551 (1995)). Although high level RNA accumulation has been achieved in some cases, a major disadvantage of such transcription units is the limited ability to regulate their expression. Also, tRNA promoters have intragenic promoter elements, resulting in RNA transcripts carrying additional tRNA sequence which may affect the folding of the adjoining functional RNA moiety.

The present invention is directed to overcoming these and other deficiencies in the art.

SUMMARY OF THE INVENTION

As used herein, the term "aptamer" refers to reagents generated in a selection from a combinatorial library (typically in vitro) wherein a target molecule, generally although not exclusively a protein or nucleic acid, is used to select from a combinatorial pool of molecules, generally although not exclusively oligonucleotides, those that are capable of binding to the target molecule. The selected reagents can be identified as primary aptamers. The term "aptamer" includes not only the primary aptamer in its original form, but also secondary aptamers derived from (i.e., created by minimizing and/or modifying) the primary aptamer. Aptamers, therefore, must behave as ligands, binding to their target molecule.

One aspect of the present invention relates to a monovalent RNA aptamer that binds to Drosophila splicing factor B52.

Another aspect of the present invention relates to a multivalent RNA aptamer that includes at least two RNA aptamer sequences linked together.

Yet another aspect of the present invention relates to an isolated or constructed DNA molecule encoding either a monovalent RNA aptamer or a multivalent RNA aptamer of the present invention.

Still another aspect of the present invention relates to an engineered gene encoding a multivalent RNA aptamer, where the engineered gene includes a DNA sequence encoding a multivalent RNA aptamer and a regulatory sequence which controls expression of the DNA sequence encoding a multivalent RNA aptamer.

Another aspect of the present invention relates to a method of expressing a multivalent RNA aptamer in a cell which includes introducing either a DNA molecule or an engineered gene of the present invention into a cell under conditions effective to express the multivalent RNA aptamer.

Yet another aspect of the present invention relates to a method of inhibiting activity of a target molecule in a cell which includes expressing a multivalent RNA aptamer in the cell, the multivalent RNA aptamer having an affinity for a target molecule sufficient to inhibit activity of the target molecule.

Another aspect of the present invention relates to a method of increasing activity of a splicing factor protein in a cell. This method includes inserting a multivalent RNA aptamer, which binds to a splicing factor protein, into an RNA transcript, which contains exons and introns, under conditions effective to enable splicing of the RNA transcript.

A further aspect of the present invention relates to a transgenic non-human organism whose somatic and germ cell lines contain an engineered gene encoding a multivalent RNA aptamer which inhibits activity of a target molecule to treat a condition associated with an expression level of the target molecule.

Additional aspects of the present invention include a constructed DNA molecule that contains a plurality of monomeric sequences each encoding a functional RNA molecule; an engineered gene that includes a DNA sequence containing a plurality of monomeric sequences each encoding a functional RNA molecule and a regulatory sequence which controls expression of the DNA sequence; and a transgenic non-human organism whose somatic and germ cell lines contain an engineered gene encoding a functional RNA molecule, where the functional RNA molecule inhibits the activity of a target molecule to treat a condition associated with an expression level of the target molecule.

Still further aspects of the invention relate to methods of expressing a functional RNA molecule in a cell by introducing either a constructed DNA molecule or an engineered gene, which encode the functional RNA molecule, into a cell under conditions effective to express the functional RNA molecule.

By coupling in vitro selection with in vivo transcriptional regulation, a multivalent RNA aptamer can be constructed that has a higher affinity for its target molecule (e.g., protein, nucleic acid, etc.) than its component RNA aptamers. When its in vivo transcription is regulated, the multivalent RNA aptamer of the present invention can be used according to a general methodology to inhibit in vivo functions of a specific target molecule. As shown herein using the Drosophila splicing factor protein B52 as a model system, a multivalent RNA aptamer of the present invention, when expressed in cells of cell culture or in somatic and germ cells of a transgenic organism, can act as a protein antagonist in vivo. When the multivalent RNA aptamer is expressed in the somatic and germ cells of a transgenic organism, activity of the target protein is inhibited to treat a condition associated with an expression level of the target protein. The multivalent RNA aptamers of the present invention have the combined advantages of prior art systems described above, but it eliminates their major shortcomings. Like antibodies, the multivalent RNA aptamers can be made to inhibit activity of specific target proteins. Like small organic molecules, multivalent RNA aptamers can directly target specific domains or discrete functional surfaces of the target protein within cells. Like conditional alleles, administration and expression of the multivalent RNA aptamers can be controlled genetically in whole organisms. In addition, expression of the multivalent RNA aptamers can be limited to specific tissues, cells, or stages of development.

BRIEF DESCRIPTION OF THE DRAWINGS

FIGS. 2A and 2B identify individual RNA sequences selected by B52 from a randomized pool and the predicted secondary structures of the B52-selected sequences. Referring to FIG. 2A, the names of the individual clones are given to the left of each selected sequence. The variable region is represented by capital letters and the shared sequence motif is represented in bold type characters. Nucleotides belonging to the flanking constant region are shown in lower case characters. Nucleotides only shared by BBS #4, 14, 15 (SEQ. ID. No. 1) and BBS #8 (SEQ. ID. No. 2) are underlined. The full sequence of the constant flanking region is shown at the bottom. The predicted secondary structures shown in FIG. 2B were generated by the computer program MulFold (Jaeger et al., "Improved Predictions of Secondary Structures for RNA," *Proc. Natl. Acad. Sci. USA* 86:7706–7710 (1989), and Zuker, "On Finding All Suboptimal Foldings of an RNA Molecule," *Science* 244:48–52 (1989), which are hereby incorporated by reference). Foldings with lowest free energy are displayed. Nucleotides forming the shared sequence motif are represented in bold type characters. Residues derived from the constant flanking region are represented in lower case characters.

As shown in FIG. 3A, the binding of B52 tightly to selected sequences is depicted in a band shift assay on a 2.5% agarose gel of 20 μl binding reactions with increasing amounts of purified B52 as indicated. GO (SEQ. ID. No. 24) is a control sequence randomly picked up from the original pool. FIG. 3B shows competitive binding of selected sequences for B52. Reactions were performed as in FIG. 3A, except that an excess amount of cold competitor RNA (as indicated) was added prior to the radioactive probes.

FIG. 4 lists the sequences used for mapping of the minimal binding elements on RNA isolated from the pool. Deletion analysis was used to define a minimal binding site and substitution mutations were used to define key features of the binding site. Anti-sense sequences of the consensus do not bind B52. Short RNA transcripts were produced by in vitro transcription and their affinity to B52 was assayed by band shift. The highest affinity (e.g., ++++) is identical to that of BBS #8. Each + sign indicates about a 3-fold difference in affinity as compared to BBS #8. The predicted secondary structure of each RNA is designated under the sequence, with paired bases denoted by matching parentheses "( )" to either side of unpaired bases marked by dashes "-". The stability of these structures is indicated by their folding energy (kcal/mole). The substituted bases are signified by italics. Although the base pairs represented by "<>" were expected for the construct bbs-II as in its parental construct BBS-II, the computer program predicted an alternative structure with negligible (0.2 kcal/mole) folding energy.

FIG. 5A contains images of RNase footprinting assays. RNase footprinting using RNase T2 (Lanes 2–4) or RNase V1 (Lanes 9–11) identifies the hairpin loop of BBS #8 (SEQ. ID. No. 2) as the B52 binding site. RNase was added to binding reactions either lacking B52 (Lanes 2 and 9), containing 2 pmole of B52 (Lanes 3 and 10), or containing 20 pmole of B52 (Lanes 4 and 11), and the resulting RNA products were analyzed by primer extension. The input RNA is shown to identify nicks in the RNA as well as reverse transcriptase stops (Lane 1). The sequencing ladder (Lanes 5–9) was used to identify the bases of interaction. FIG. 5B contains a corresponding diagram which illustrates the localization of the B52-binding site on a predicted secondary structure of BBS #8 (SEQ. ID. No. 2). Open circles indicate weak T2 protection and filled circles and squares indicate strong T2 and V1 protection, respectively. The single-stranded regions and the sequence in the stem of the hairpin loop structure are indicated next to the sequencing ladder by thin and thick lines, respectively. The sequence of BBS #8 is indicated by the nucleotides and the constant flanking region and vector sequences depicted by a skeletal diagram.

FIG. 7 is a list of the engineered genes of the present invention. Different combinations of promoters and transcriptional templates, which vary by length and orientation, are listed. The number of BBS's contained in a transcriptional template is indicated in its name as the product of the numbers within the parentheses. For example, BBS(5.12) has 60 BBS units in twelve pentavalent monomers. A minus sign indicates antisense, Hic stands for "heat inducible cassette," and Mtn stands for "metallothionein."

FIG. 8A shows the sequence and free-energy-minimized secondary structure of the monomeric unit of an immature pentavalent RNA transcript (i.e., from a multimeric RNA transcript). Parts of the selected aptamers are incorporated into the construct in their original or modified form. The original aptamer sequences are enclosed in the boxes. Bold type letters indicate important functional sequences as annotated. FIG. 8B shows the sequence and free-energy-minimized secondary structure of the mature pentavalent RNA aptamer having an affinity for Drosophila B52. After self-cleavage of the immature pentavalent RNA transcript, the residual sequence of the ribozyme at both the 5' and 3 ends of the molecule is brought together to form a virtually closed structure. The stem formed between the 3' and 5' termini, the S35 motif, is enclosed in a box. Both structures in FIGS. 8A and 8B are generated by the computer program MulFold (Jaeger et al., "Improved Predictions of Secondary Structures for RNA," *Proc. Natl. Acad. Sci. USA* 86:7706–7710 (1989), and Zuker, "On Finding All Suboptimal Foldings of an RNA Molecule," *Science* 244:48–52 (1989), which are hereby incorporated by reference). Foldings with lowest free energy are displayed.

FIGS. 9A and 9B are images depicting the result of binding assays which illustrates the avidity of the mature pentavalent RNA aptamer for B52. FIG. 9A compares the avidity of the mature pentavalent RNA aptamer for B52 to the affinity of a single aptamer. A template containing a single pentavalent monomeric unit, P1-2-3/BBS(5.1), was transcribed in both orientations to produce the probes BBS (5+) and BBS(5−). Their avidity to B52 was compared with the affinity of BBS#14 in a band shift assay. The adjacent lanes in each set have a 10-fold difference in B52 concentration, the lowest being 5 nM. The molar ratio of pentamer to monomer used in different sets was 1:5, so that the concentration of BBS units was identical in each reaction. The efficiency of ribozyme cleavage was also assessed on this 25 cm native agarose gel. The uncut transcript of BBS(5+), the Fragment A, and the Fragment C are indicated by U, A, and C, respectively. FIG. 9B illustrates a band shift assay with RNA transcribed from templates with different length and orientations. The length of the templates are indicated by the number of the monomeric units located after the decimal point in the parentheses. The number of BBS's contained in a template is the product of the numbers within the parentheses. The orientation of the template is indicated by a plus or minus sign. Fragment C is indicated. The assignments of bands representing Fragments A and B are mainly based on their mobility and intensity, and are not unambiguous due to the possible alternative conformations of RNA fragments and their different movement on this native gel.

FIG. 10A illustrates a 5% polyacrylamide 7 M urea preparative gel, loading 20 µl overnight transcription reaction mixture in two lanes. Fragments A and B are indicated. The small Fragment C ran off the gel. "Actin" RNA was transcribed from a plasmid having a fragment of the mouse-actin gene inserted in the antisense orientation under the transcriptional control of T7 promoter, and provided as a control template in the MAXIscript kit (Ambion). Its transcript is 334-nt in length. The RNA was visualized by UV shadowing and the bands representing Fragment B were excised and eluted. FIG. 10B illustrates a gel purified mature pentavalent RNA aptamer as a competitor in a binding reaction. BBS #8, the strongest-binding monovalent aptamer, was used as the probe in a gel shift assay with gel purified mature pentavalent RNA aptamer and its antisense RNA, BBS(5−), as competitors. The same amount of purified Torulla yeast RNA (Ambion) consisting of fragments of 300–500 bases (yRNA) was used as a control.

FIG. 11A illustrates suppression of B52 function by mature pentavalent RNA in trans. Labeled fiz pre-mRNA was used as the substrate in a splicing assay, in which B52 complements the splicing-deficient S100 extract. This activity was challenged by adding the gel purified mature pentavalent RNA (Fragment B), its antisense RNA (BBS(5−)), or purified yeast RNA. FIG. 11B illustrates creation of a B52-specific splicing enhancer with BBS in cis. ftz+BBS(5) was tested in a splicing assay containing S100 extract with or without increasing amounts of B52. The original ftz without BBS and a ftz derivative with the antisense sequence of BBS(5),ftz-BBS(5), were used as controls. Splicing products and intermediates of ftz are indicated schematically between the two gels and those of ftz+BBS(5) are indicated to the right of FIG. 11B. Exons are represented by boxes, introns by lines, BBS(5) by filled boxes.

FIGS. 12A and 12B are images which illustrate in vivo expression of mature pentavalent RNA aptamer specific for B52. FIG. 12A illustrates transient expression of mature pentavalent RNA aptamer in Drosophila S2 cell cultures. The transcriptional templates BBS(5.2) and BBS(5.12) were driven by a heat shock promoter and a metallothionein promoter, respectively. Steady-state mature pentavalent RNA aptamer levels without induction and peak level after induction (90° heat shock or 24 hour $Cu^{2+}$) were compared. To measure the half-life of the mature pentavalent RNA aptamer, actinomycin D was added to the media immediately after the 90° heat shock treatment, and total RNA was prepared at the time indicated. FIG. 12B illustrates expression of the mature pentavalent RNA aptamer in transgenic flies. HicBBS(5.12) is a homozygous strain containing the engineered gene bearing the same name used in the transient expression experiments. hsGAL4-UASBBSs are heterozygous flies generated by mating different UASBBS transgenic strains (length and orientation of the BBS constructs as indicated) with the strain containing the transgene hsGAL4, which is driven by a heat shock promoter. RNA samples were prepared from third instar larvae with and without heat treatment. The mature pentavalent RNA aptamer standards were transcribed in vitro and gel purified. The mature pentavalent RNA aptamer in these samples was measured by RNase protection assay with a probe covering part of the monomeric pentavalent unit.

FIGS. 13A and 13B are images which illustrate in situ visualization of the transgene encoding the mature pentavalent RNA aptamer, its expression, and its binding to B52. FIG. 13A illustrates subcellular localization of the mature pentavalent RNA aptamer. A Texas Red labeled RNA probe was used to visualize the mature pentavalent RNA aptamer in the nuclei of whole mount salivary glands in late third instar larvae of the HicBBS(5.12) transgenic line after heat treatment. The mature pentavalent RNA aptamer is seen to fill the intranuclear space between the giant polytene chromosomes. DNA was stained with 4',6-diamidino-2-phenylindole (DAPI). FIG. 13B illustrates the mapping of the transgene in the HicBBS(5.12) strain to locus 12A on the X chromosome (left panel). After heat induction, the expression of the mature pentavalent RNA aptamer resulted in a medium sized puff (middle panel). B52 was strongly recruited to this site (right panel). The transgene and its expression were visualized using the same probe as in FIG. 13A. B52 was visualized by immunofluorescence with an anti-B52 antibody. The images were pseudo-colored in red and merged with those of DAPI stained chromosomes (pseudo-colored in cyan) to facilitate the localization. The transgenic insertion site is indicated by a white arrow head in each panel. The major heat shock loci at 87A and 87C are indicated by white dots in the right panel.

FIGS. 15A and 15B illustrate transgenic fly lines and the phenotypic effects of pentavalent RNA aptamer expression. FIG. 15A is schematic depicting self-crossed, double-balanced fly strains. FIG. 15B is a chart showing the reduced viability caused by continuous high level expression of the mature pentavalent RNA aptamer. The genotype of the isogenetic double transgenic flies are shown in FIG. 15A. Each pair has a hsGAL4-UASBBS line and a UASBBS-UASBBS line. The only difference between the two lines is the chromosome carrying hsGAL4 in one line is replaced by a chromosome carrying an UASBBS in the other. Selfing the double balanced stocks of both lines, as shown in FIG. 15A, yielded four different genotypes among the progeny with different copy number of hsGAL 4 and UASBBS, as tabulated. The viability is calculated as the percentage of surviving BBS-expressing progeny with regard to its isogenetic counterparts in which BBS is dormant.

FIGS. 17A–17K illustrate the effects on phenotypes of B52 overexpression with the co-expression of mature pentavalent RNA aptamer. FIG. 17A depicts a generic mating scheme used to prepare transgenic flies. Active transcription of the UASB52 transgene and/or the UASBBS(5.12) transgene is indicated by the names of gene product in braces. The parental transgenic strains used to synthesize the double transgenic UASB52-UASBBS strain were used in {B52} and {BBS} controls. Despite decreased viability, the surviving {BBS} flies were morphologically normal. FIGS. 17B–17D are images of salivary glands dissected from third instar larvae and FIGS. 17E–17G are images of bristles appearing on the adult notum. FIG. 17H is a chart showing a comparison of the phenotypes of the three classes of progeny. Different GAL4 sources were used to drive the overexpression of B52 and the expression of BBS (5.12). FIG. 17I depicts a generic mating scheme used to prepare transgenic flies, which overexpress B52 and co-express the mature pentavalent RNA aptamer. The use of the double balanced hsGAL4-UASB52 strain produced three other genotypes among the progeny that serve as internal controls for quantitation. Two sets of independent transformants of each BBS construct were used in the crosses. FIGS. 17J and 17K are graphs which illustrate the effects of different dosages of BBS expression and a constant dosage of B52 overexpression, both driven by the hsGAL4 transgene. Twenty female adults were scored to assess bristle development. Error bars indicate one standard deviation on each side of the mean.

DETAILED DESCRIPTION OF THE INVENTION

Figure 1:
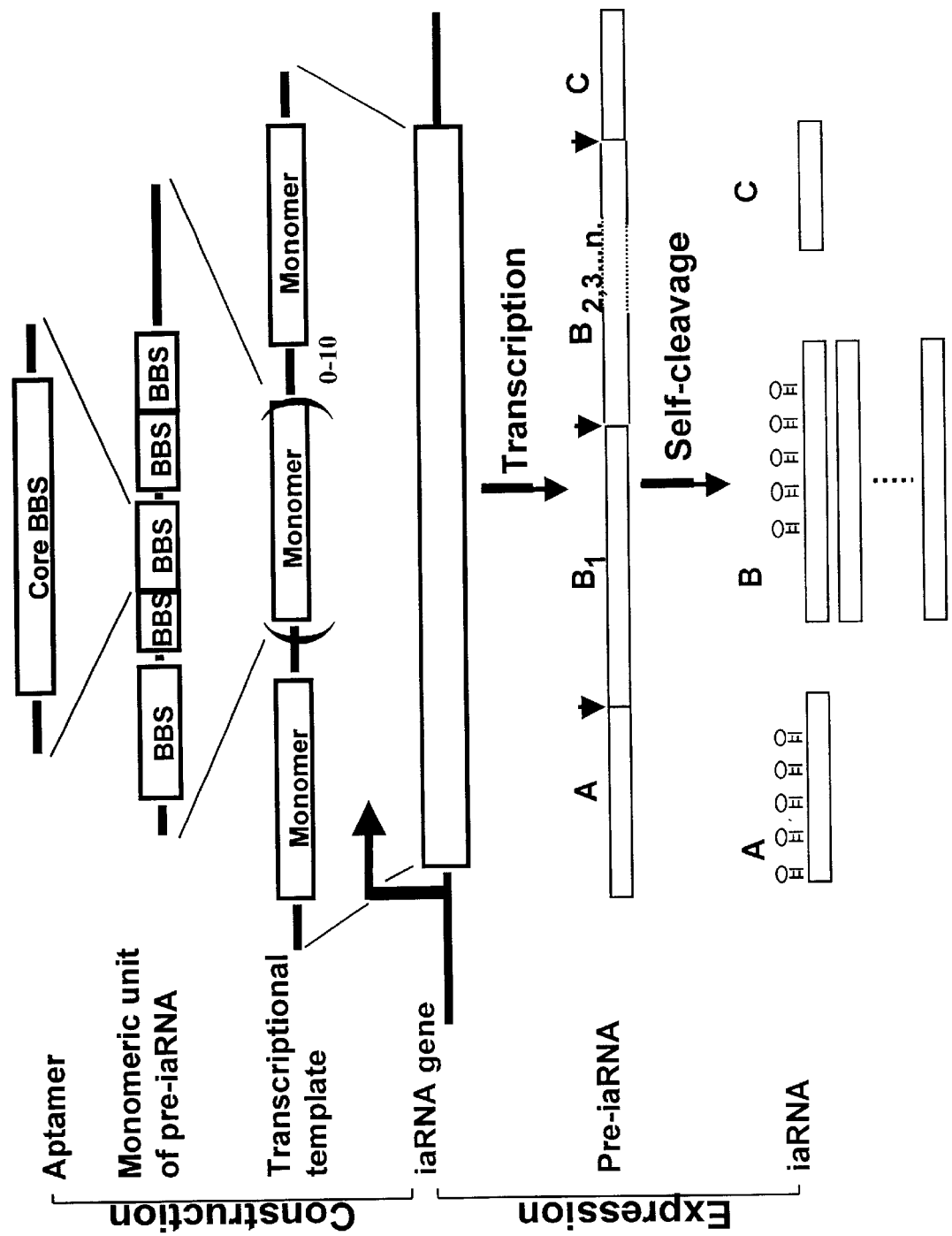
FIG. 1 is a schematic diagram depicting the construction and expression of an engineered gene of the invention which encodes the multimeric immature RNA transcript. The construction phase shows the polymerization of hierarchically encapsulated sequence units in four levels: the primary RNA aptamer sequence, the monomeric unit, the transcriptional template, and the iaRNA gene. In the expression phase, the major functional elements on each level, including the promoter, the hammerhead ribozyme, and the hairpin structure, are indicated symbolically.

One aspect of the present invention relates to a novel monovalent RNA aptamer that binds to a splicing factor ("SR") protein. SR proteins are structurally and functionally related and evolutionarily conserved. The SR family contains at least six members, which are conserved from *Drosophila melanogaster* to humans (Zahler et al., "SR Proteins: A Conserved Family of Pre-mRNA Splicing Factors," *Genes Dev.* 6:837–847 (1992), which is hereby incorporated by reference). The splicing factor protein is preferably the Drosophila splicing factor B52, more preferably B52 from *Drosophila melanogaster*. B52 from *Drosophila melanogaster* is homologous to the human splicing factor SRp55 (Champlin et al., "Characterization of a Drosophila Protein Associated with Boundaries of Transcriptionally-Active Chromatin," *Genes Dev.* 5:1611–1621 (1991), which is hereby incorporated by reference).

The Drosophila SR protein family, which includes B52, is a group of nuclear proteins that are both essential splicing factors and specific splicing regulators (Fu, "The Superfamily of Arginine/Serine-Rich Splicing Factors," *RNA* 1:663–680 (1995); Manley and Tacke, "SR Proteins and Splicing Control," *Genes Dev.* 10(3):1569–1579 (1996), which are hereby incorporated herein by reference). Like most other SR proteins, B52 contains two RNA recognition motifs ("RRMs") in the N-terminus and a C-terminal domain rich in serine-arginine dipeptide repeats (Champlin et al., "Characterization of a Drosophila Protein Associated With Boundaries of Transcriptionally Active Chromatin," *Genes Dev.* 5:1611–1621 (1991), which is hereby incorporated by reference). In vivo, B52 is an abundant protein and plays a critical role in Drosophila development. B52 deletion mutants are homozygous lethal at the second-instar larval stage (Ring and Lis, "The SR Protein B52/SRp55 is Essential for Drosophila Development," *Mol. Cell. Biol.* 14:7499–7506 (1994), which is hereby incorporated by reference), and overexpression of B52 protein causes severe developmental defects (Kraus and Lis, "The Concentration of B52, an Essential Splicing Factor and Regulator of Splice Site Choice, is Critical for Drosophila Development," *Mol. Cell. Biol.* 14:5360–5370 (1994), which is hereby incorporated by reference), evincing that B52 is an essential protein which must be expressed at the appropriate level.

Suitable monovalent RNA aptamers which bind Drosophila splicing factor B52 are listed below and in FIG. 3A. A first monovalent RNA aptamer, designated BBS#4,14,15, has a nucleotide sequence corresponding to SEQ. ID. No 1 as follows:

gggagaauuc aacugccauc uaggcagggu aacgaucaac cuggcgacag cugcccugcc 60
guccaaguac uacaagcuuc uggacucggu 90

A second monovalent RNA aptamer, designated BBS#8, has a nucleotide sequence corresponding to SEQ. ID. No. 2 as follows:

gggagaauuc aacugccauc uaggcugguc aaccaggcga ccgccacccg cgcgcgcaau 60
accuaguacu acaagcuucu ggacucggu 89

A third monovalent RNA aptamer, designated BBS#1 1, has a nucleotide sequence corresponding to SEQ. ID. No. 3 as follows:

gggagaauuc aacugccauc uaggcugcuc acgaguccau gaccaguacg aucaaccagg 60
cgacaguacu acaagcuucu ggacucggu 89

A fourth monovalent RNA aptamer, designated BBS#23, has a nucleotide sequence corresponding to SEQ. ID. No. 4 as follows:

gggagaauuc aacugccauc uaggcccaac ugcuaagaag cauccuguac gaucaacccg 60
gcgacaguac uacaagcuuc uggacucggu 90

The monovalent RNA aptamers of the present invention, which are specific for B52, were identified from a large pool of RNA molecules. Identifying the primary aptamers basically involved selecting RNA aptamers that bind full-length B52 with high affinity ($K_d$=20–50 nM) and specificity from a large pool of RNAs containing a random region of about 40 bases (Shi et al., "A Specific RNA Hairpin Loop Structure Binds the RNA Recognition Motifs of the Drosophila SR Protein B52," *Mol. Cell. Biol.* 17:1649–1657 (1997); Shi, "Perturbing Protein Function with RNA Aptamers," Thesis, Cornell University, University Microfilms, Inc. (1997), which are hereby incorporated by reference). Both RRMs of the protein are required for the interaction with the RNA aptamer. The B52 binding sites ("BBS") on members of this non-clonally derived family of RNA aptamers not only have a well "conserved" consensus sequence, but also have a virtually identical hairpin loop structure as predicted by the MulFold computer program using free energy minimization (Jaeger et al., "Improved Predictions of Secondary Structures for RNA," *Proc. Natl. Acad. Sci. USA* 86:7706–7710 (1989), and Zuker, "On Finding All Suboptimal Foldings of an RNA Molecule," *Science* 244:48–52 (1989), which are hereby incorporated by reference) and confirmed by structure-specific enzymatic probing using RNase, see Example 3 infra. The conserved sequence of the above-identified monovalent RNA aptamers of the present invention has a nucleotide sequence of SEQ. ID. No. 5 as follows:

gnucaaccng gcgacng 17

Of this sequence identified as SEQ. ID. No. 5, nucleotides 5–12 form the functional loop structure of the predicted hairpin loop secondary structure of each monovalent RNA aptamer.

To identify primary aptamers of any particular target protein, an established in vitro selection and amplification scheme, SELEX, can be used. The SELEX scheme is described in detail in U.S. Patent No. 5,270,163 to Gold et al.; Ellington and Szostak, "In vitro Selection of RNA Molecules That Bind Specific Ligands," *Nature* 346:818–822 (1990); and Tuerk and Gold, "Systematic Evolution of Ligands by Exponential Enrichment: RNA Ligands to Bacteriophage T4 DNA Polymerase," *Science* 249:505–510 (1990), which are hereby incorporated by reference. An established template-primer system (Bartel et al., "HIV-1 Rev Regulation Involves Recognition of Non-Watson-Crick Base Pairs in Viral RNA," *Cell* 67:529–536 (1991), which is hereby incorporated by reference) can be adapted to produce RNA molecules having a stretch of about 38–40 random bases sandwiched between 5' and 3' constant regions. The 5' DNA template, which contains a T7 promoter used to drive transcription of the variable RNA, has a nucleotide sequence corresponding to SEQ. ID. No. 6 as follows:

gtaatacgac tcactatagg gagaattcaa ctgccatcta ggc 43

The 3' DNA template has a nucleotide sequence corresponding to SEQ. ID. No. 7 as follows:

agtactacaa gcttctggac tcggt 25

Commercial oligonucleotide synthesis generally yields more than 500 picomoles of the template at the 200 nmol synthesis scale. The synthetic oligonucleotide templates can be amplified by polymerase chain reaction ("PCR") and then transcribed to generate the original RNA pool. Assuming that ten percent of the RNA molecules are free of chemical lesions that prevent second-strand synthesis and transcription, this pool would contain more than $3 \times 10^{13}$ different sequences. Because filter binding is applicable for most protein targets, it can be used as the partitioning device, although other suitable schemes can be used. The selected primary RNA aptamers can be cloned into any conventional subcloning vector and sequenced using any variation of the dideoxy method. Next, the secondary structure of each primary RNA aptamer can be predicted by computer programs such as MulFold (Jaeger et al., "Improved Predictions of Secondary Structures for RNA," *Proc. Natl. Acad. Sci. USA* 86:7706–7710 (1989), and Zuker, "On Finding All Suboptimal Foldings of an RNA Molecule," *Science* 244:48–52 (1989), which are hereby incorporated by reference). Secondary structures of the four monovalent RNA aptamers of the present invention are shown in FIG. 3B. Mutational studies can be conducted by preparing substitutions or deletions to map both binding sites on the RNA aptamer and its target molecule, as described in Example 2 infra.

Other known RNA aptamers include, without limitation, RNA ligands of T4 DNA polymerase, RNA ligands of HIV reverse transcriptase, RNA ligands of bacteriophage R17 coat protein, RNA ligands for nerve growth factor, RNA ligands of HSV-1 DNA polymerase, RNA ligands of *Escherichia coli* ribosomal protein S1, and RNA ligands of HIV-1 Rev protein (U.S. Pat. No. 5,270,163 to Gold et al., which is hereby incorporated by reference); RNA ligands of *Bacillus subtillus* ribonuclease P (U.S. Pat. No. 5,792,613 to Schmidt et al., which is hereby incorporated by reference); RNA ligands of ATP and RNA ligands of biotin (U.S. Pat. No. 5,688,670 to Szostak et al., which is hereby incorporated by reference); RNA ligands of prion protein (Weiss et al., "RNA Aptamers Specifically Interact with the Prion Protein PrP," *J. Virol.* 71(11):8790–8797 (1997), which is hereby incorporated by reference); RNA ligands of hepatitis C virus protein NS3 (Kumar et al., "Isolation of RNA Aptamers Specific to the NS3 Protein of Hepatitis C Virus from a Pool of Completely Random RNA," *Virol.* 237(2):270–282 (1997); Urvil et al., "Selection of RNA Aptamers that Bind Specifically to the NS3 Protein of Hepatitis C Virus," *Eur. J. Biochem.* 248(1):130–138 (1997); Fukuda et al., "Specific RNA Aptamers to NS3 Protease Domain of Hepatitis C Virus," *Nucleic Acids Symp. Ser.* 37:237–238 (1997), which are hereby incorporated by reference); RNA ligands of chloramphenicol (Burke et al., "RNA Aptamers to the Peptidyl Transferase Inhibitor Chloramphenicol," *Chem. Biol.* 4(11):833–843 (1997), which is hereby incorporated by reference); RNA ligands of the adenosine moiety of S-adenosyl methionine (Burke and Gold, "RNA Aptamers to the Adenosine Moiety of S-Adenosyl Methionine: Structural Inferences from Variations on a Theme and the Reproducibility of SELEX," *Nucleic Acids Res.* 25(10):2020–2024 (1997), which is hereby incorporated by reference); RNA ligands of protein kinase C (Conrad et al., "Isozyme-Specific Inhibition of Protein Kinase C by RNA Aptamers," *J. Biol. Chem.* 269(51):32051–32054 (1994); Conrad and Ellington, "Detecting Immobilized Protein Kinase C Isozymes with RNA Aptamers," *Anal. Biochem.* 242(2):261–265 (1996), which are hereby incorporated by reference); RNA ligands of subtilisin (Takeno et al., "RNA Aptamers of a Protease Subtilisin," *Nucleic Acids Symp. Ser.* 37:249–250 (1997), which is hereby incorporated by reference); RNA ligands of yeast RNA polymerase II (Thomas et al., "Selective Targeting and Inhibition of Yeast RNA Polymerase II by RNA Aptamers," *J. Biol. Chem.* 272(44):27980–27986 (1997), which is hereby incorporated by reference); RNA ligands of human activated protein C (Gal et al., "Selection of a RNA Aptamer that Binds to Human Activated Protein C and Inhibits its Protein Function," *Eur. J. Biochem.* 252(3):553–562 (1998), which is hereby incorporated by reference); and RNA ligands of cyanocobalamin (Lorsch and Szostak, "In vitro Selection of RNA Aptamers Specific for Cyanocobalamin," *Biochem.* 33(4):973–982 (1994), which is hereby incorporated by reference). Additional RNA aptamers are continually being identified and isolated by those of ordinary skill in the art.

Another aspect of the present invention relates to a multivalent RNA aptamer that contains at least two RNA aptamer sequences linked together.

The multivalent RNA aptamer of the present invention is prepared from known RNA aptamers or those identified using, for example, the SELEX procedure described above. Once the sequence and structure information of the individual RNA aptamers has been identified, a multivalent RNA aptamer of the present invention can be designed.

Multivalent RNA aptamers of the present invention should enhance the stability of the target molecule-RNA interaction, because it is equivalent to an increased local concentration of aptamers for the target molecule that binds to RNA, thus providing a decreased overall off rate. Many RNA aptamers have distinct secondary structures such as hairpin loops (see FIG. 3B), and correct folding of each individual aptamer in an array is critical. To avoid unwanted pairing of sequences in the stem of the individual RNA aptamers (i.e., to achieve an overall multivalent RNA aptamer structure that is both kinetically favored and thermodynamically stable), the stem of some individual RNA aptamers can be reinforced and/or elongated with different sequences to reduce the general sequence similarity among them. Energy-minimized secondary structures can be generated using any conventional program, such as the Mulfold program (Jaeger et al., "Improved Predictions of Secondary Structures for RNA," *Proc. Natl. Acad. Sci. USA* 86:7706–7710 (1989), and Zuker, "On Finding All Suboptimal Foldings of an RNA Molecule," *Science* 244:48–52 (1989), which are hereby incorporated by reference). The secondary structures for both monomeric unit of the immature RNA transcript and the mature multivalent aptamer can be generated and the folding pattern of individual moieties can be compared to the previously established folding pattern of the monovalent RNA aptamer(s). The sequence of these monomeric units can then be adjusted iteratively until each individual aptamer (i.e., in the immature RNA transcript and the mature multivalent RNA aptamer) is folded correctly.

Each of the at least two RNA aptamer sequences preferably has a hairpin loop structure, with a neck portion of various lengths that is characterized by a high degree of base-pairing and a loop portion that is characterized by non-paired bases of a target-binding sequence.

In addition to the target-binding region of the individual RNA aptamers, which together form the major functional sequence of the mature multivalent RNA aptamer, different regulatory sequences or structural elements can be incorporated into the mature multivalent RNA aptamer as ancillary sequences. A preferred ancillary sequence is an exonuclease-blocking sequence linked to one of the at least two RNA aptamer sequences.

In particular, a stable tetra-loop near the 3' end of the mature, multivalent RNA aptamer can be engineered. Because of its highly stacked and relatively inaccessible structure, the UUCG tetra-loop (Cheong et al., "Solution Structure of an Unusually Stable RNA Hairpin, 5'GGAC (UUCG)GUCC," *Nature*346:680–682 (1990), which is hereby incorporated by reference) is included to stabilize the mature multivalent RNA aptamer against degradation by 3' exonucleases and to serve as a nucleation site for folding (Varani, "Exceptionally Stable Nucleic Acid Hairpins," *Annu. Rev. Biophys. Biomol. Struct.* 24:379–404 (1995), which is hereby incorporated by reference).

In addition, the mature multivalent RNA aptamer can contain an "S35 motif" which yields a virtually closed structure resistant to nucleolytic degradation. The S35 motif, constructed by creating complementary 5' and 3' ends, has been shown to cause an over 100-fold increase in accumulation of a tRNA-ribozyme chimerical transcript in stably transduced cell lines (Thompson et al., "Improved Accumulation and Activity of Ribozymes Expressed from a tRNA-based RNA Polymerase III Promoter," *Nucleic Acids Res.* 23:2259–2268 (1995), which is hereby incorporated by reference).

By way of example, a preferred mature multivalent RNA aptamer of the present invention is a pentavalent RNA aptamer that includes five tandemly arranged RNA aptamer sequences which bind to the Drosophila splicing factor B52, a UUCG tetraloop, and an S35 motif (FIG. 3B). By combining the various monovalent RNA aptamers of the present invention to create a pentavalent RNA aptamer, it was possible to create an aptamer having higher avidity for B52. The five tandemly arranged RNA aptamer sequences correspond to BBS #11 (SEQ. ID. No. 3), BBS #23 (SEQ. ID. No. 4), two copies of BBS #8 (SEQ. ID. No. 2), and BBS #4, 14, 15 (SEQ. ID. No. 1). Each of the five tandemly arranged RNA aptamer sequences has a hairpin loop structure that has a neck portion of various lengths and a loop portion. Specifically, each of the loop portions contains nucleotides 5–12 of SEQ. ID. No. 5 as non-paired bases. The nucleotide sequence for the mature multivalent RNA aptamer corresponds to SEQ. ID. No. 8 as follows:

gcggccgccu ccgcggccgc cugaugaguc cgugaggacg aaa-caugcau gucgagagua 60 cgaucaacca ggcgacagua cucucgacga ucaaccaggc gacaguggcu ggucaaccag 120
gcgaccgcca cugcagggua acggucaacc aggcgaccgu uacccg-gacg gucaaccagg 180 cgaccguuga cuucggucag ucgagaugca uguc 214

Once the structure and sequence of the multivalent RNA aptamer has been established, a gene capable of encoding such an RNA aptamer can be prepared. Therefore, another aspect of the present invention relates to a DNA molecule and, more particularly, a gene which encodes the RNA aptamers of the present invention.

According to one embodiment, the DNA molecule encodes a monovalent RNA aptamer of the present invention.

One such DNA molecule encodes the monovalent RNA aptamer BBS#4,14,15 and has a nucleotide sequence corresponding to SEQ. ID. No. 9 as follows:

gtaatacgac tcactatagg gagaattcaa ctgccatcta ggcagggtaa cgatcaacct 60
ggcgacagct gccctgccgt ccaagtacta caagcttctg gactcggt 108

Another such DNA molecule encodes the monovalent RNA aptamer BBS#8 and has a nucleotide sequence corresponding to SEQ. ID. No. 10 as follows:

gtaatacgac tcactatagg gagaattcaa ctgccatcta ggctggtcaa ccaggcgacc 60
gccacccgcg cgcgcaatac ctagtactac aagcttctgg actcggt 107

Another such DNA molecule encodes the monovalent RNA aptamer BBS#11 and has a nucleotide sequence corresponding to SEQ. ID. No. 11 as follows:

gtaatacgac tcactatagg gagaattcaa ctgccatcta ggctgctcac gagtccatga 60
ccagtacgat caaccaggcg acagtactac aagcttctgg actcggt 107

Still another such DNA molecule encodes the monovalent RNA aptamer BBS#23 and has a nucleotide sequence corresponding to SEQ. ID. No. 12 as follows:

gtaatacgac tcactatagg gagaattcaa ctgccatcta ggcccaactg ctaagaagca 60
tcctgtacga tcaacccggc gacagtacta caagcttctg gactcggt 108

According to another embodiment, the DNA molecule encodes a multivalent RNA aptamer of the present invention. For DNA molecules encoding a multivalent RNA aptamer, it is preferable for the DNA molecule to contain a plurality of monomeric DNA sequences ligated "head-to-tail", each of which encodes a multivalent RNA aptamer. This is particularly useful for augmenting the number of multivalent RNA aptamers produced during each transcriptional event. By plurality, it is intended that the number of monomeric DNA sequences be at least two, preferably at least four, more preferably at least eight, and most preferably at least twelve. Such tandemly arrayed sequences are known to be relatively stable in bacteria (Lindquist, "Varying Patterns of Protein Synthesis in Drosophila During Heat Shock: Implications for Regulation," *Dev. Biol.* 77:463–479 (1980), which is hereby incorporated herein by reference) and can persist for many generations in transgenic fly lines (Xiao and Lis, "A Consensus Sequence Polymer Inhibits in vivo Expression of Heat Shock Genes," *Mol. Cell. Biol.* 6:3200–3206 (1986); Shopland and Lis, "HSF Recruitment and Loss at Most Drosophila Heat Shock Loci is Coordinated and Depends on Proximal Promoter Sequences," *Chromosoma* 105:158–171 (1996), which are hereby incorporated by reference). This strategy should be applicable to other organisms. For example, long direct repeating sequences have been used in yeast (Robinett et al., "In vivo Localization of DNA Sequences and Visualization of Large-scale Chromatin Organization Using lac Operator/Repressor Recognition," *J. Cell. Biol.* 135:1685–700 (1996), which is hereby incorporated by reference). It should be apparent to those of ordinary skill in the art, however, that the number of monomeric DNA sequences can vary for each application of the DNA molecule.

Depending upon the desired application and intended use for the DNA molecule, it is possible to produce homopolymers containing a plurality of substantially identical monomeric DNA sequences or copolymers containing a plurality of substantially different monomeric DNA sequences. The mature multivalent RNA aptamers produced from such a homopolymer are a single type, each capable of inhibiting the activity of the same target. In contrast, the mature multivalent RNA aptamers produced from such a copolymer are different types, each capable of inhibiting the activity of a distinct target or, alternatively, binding to discrete surfaces of the same target. Thus, the plurality of monomeric DNA sequences can be substantially identical (i.e., producing substantially the same multivalent RNA aptamer) or they can be substantially different (i.e., producing substantially different multivalent RNA aptamers). When the plurality of monomeric DNA sequences are substantially different, the resulting RNA multivalent aptamers can be directed to the same or to different target molecules.

When the DNA molecule encodes a plurality of monomeric DNA sequences, it is important that the resulting RNA transcript be cleaved into the individual multivalent RNA aptamers. To this end, it is particularly desirable for each of the plurality of monomeric DNA sequences to also encode a cis-acting ribozyme that can cleave the immature RNA transcript of the DNA molecule to yield multiple copies of the mature multivalent RNA aptamers. Although any ribozyme sequence can be utilized, a hammerhead ribozyme sequence (Haseloff and Gerlach, "Simple RNA Enzymes with New and High Specific Endoribonucleases Activities," *Nature* 334:585–591 (1988), which is hereby incorporated by reference) is preferred because of its simplified and efficient structure. The sequence encoding the hammerhead ribozyme is incorporated into each of the plurality of monomeric DNA sequences, resulting in the hammerhead ribozyme being located at the 3' end of each monomeric unit of the immature RNA transcript. The immature RNA transcript is self-cleaved by the cis-acting ribozyme to yield the mature multivalent RNA aptamer.

When the DNA molecule is a polymer encoding an immature RNA transcript containing more than one multivalent RNA aptamer, this self-cleavage produces three different kind of RNA fragments of the immature RNA transcript, as shown in FIG. 1. Fragment A contains the target-binding region, the tetra-loop, and a portion of the ribozyme sequence, while fragment C is the terminal fragment of the immature RNA transcript and has no aptamer sequence. Fragment B is the mature multivalent RNA aptamer molecule of the present invention, which is expected to fold into a stable structure when an eight base pair stem forms following the cleavage (i.e., by the ribozyme) and holds both 5' and 3' ends together in the S35 motif as described above. The structure of a mature pentavalent RNA aptamer specific for Drosophila B52 (SEQ. ID. No. 8) is shown in FIG. 3B. The molar fraction of Fragment B in the cleavage product increases in proportion to the number of monomeric DNA sequences contained in the template.

One such DNA molecule of the present invention is a monomer which encodes an immature pentavalent RNA aptamer and has a nucleotide sequence corresponding to SEQ. ID. No. 13 as follows:

gtcgagagta cgatcaacca ggcgacagta ctctcgacga tcaaccaggc gacagtggct 60
ggtcaaccag gcgaccgcca ctgcagggta acggtcaacc aggcgaccgt tacccggacg 120
gtcaaccagg cgaccgttga cttcggtcag tcgagatgca tgtcgcggcc gcctccgcgg 180
ccgcctgatg agtccgtgag gacgaaacat gcat 214

The nucleotide sequence for the monomeric immature RNA transcript encoded by this DNA molecule corresponds to SEQ. ID. No. 14 as follows:

gucgagagua cgaucaacca ggcgacagua cucucgacga ucaaccaggc gacaguggcu 60
ggucaaccag gcgaccgcca cugcagggua acggucaacc aggcgaccgu uacccggacg 120
gucaaccagg cgaccguuga cuucggucag ucgagaugca ugucgcggcc gccuccgcgg 180
ccgccugaug aguccgugag gacgaaacau gcau 214

Figure 3A:
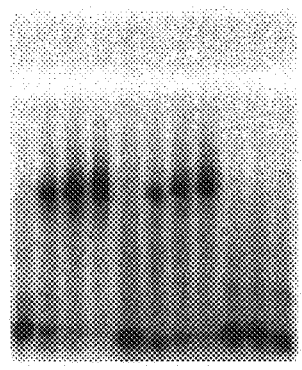
FIGS. 3A and 3B are images which show the affinity and specificity of B52-binding RNA aptamers.
Figure 3B:
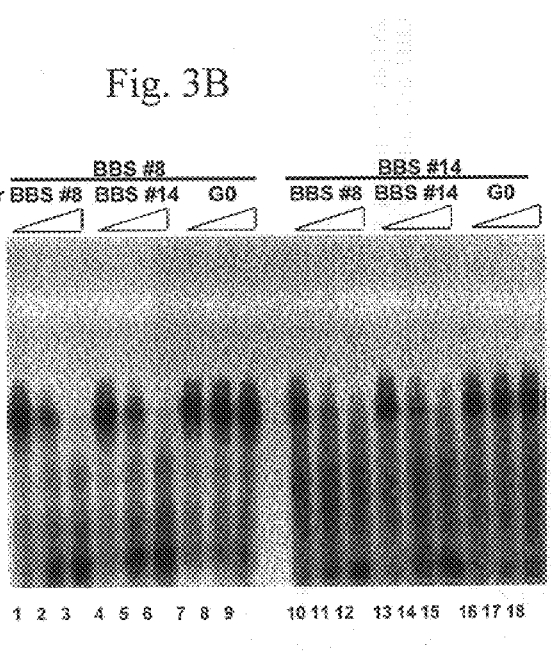
Figure 5A:
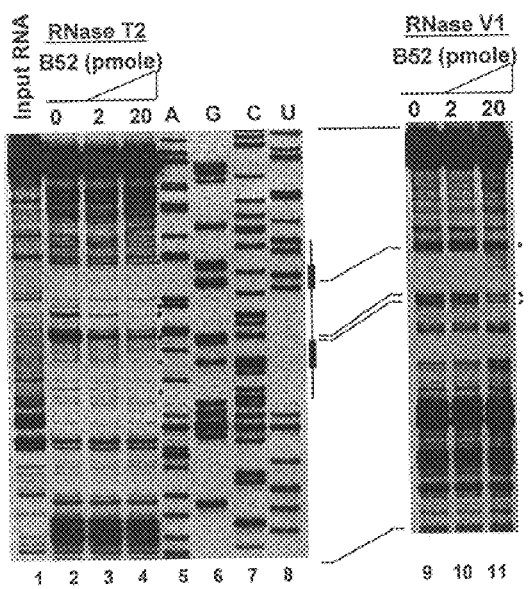
FIGS. 5A and 5B identify the active domain for B52 binding on BBS #8.
Figure 5B:
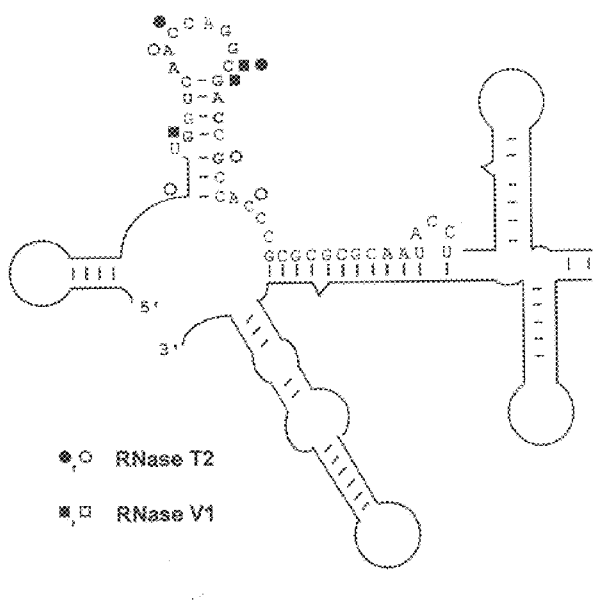

The structure of this immature RNA transcript is shown in FIG. 3A.

Once the DNA molecule of the present invention has been constructed, it can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for the transcription of the RNA molecule of the present invention.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant or engineered genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference), and any derivatives thereof. Suitable vectors are continually being developed and identified. Recombinant molecules can be introduced into cells via transformation, transduction, conjugation, mobilization, or electroporation. The DNA sequences are cloned into the vector using standard cloning procedures in the art, as described by Maniatis et al., Molecular Cloning: A Laboratory Manual, Cold Springs Laboratory, Cold Springs Harbor, N.Y. (1982), which is hereby incorporated by reference.

A variety of host-vector systems may be utilized to express the monovalent RNA aptamer-encoding sequence(s) or the multivalent RNA aptamer-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Transcription of the DNA molecule of the present invention is dependent upon the presence of a promoter which is a DNA sequence that directs the binding of RNA polymerase and thereby promotes RNA synthesis. The DNA sequences of eukaryotic promoters differ from those of procaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). For the purposes of expressing the constructed DNA molecule or engineered gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription in procaryotic cells. These transcription initiation signals may vary in "strength" as measured by the quantity of gene specific messenger RNA and protein synthesized, respectively. The DNA expression vector, which contains a promoter, may also contain any one of various "strong" transcription initiation signals.

Once the constructed DNA molecules encoding the monovalent RNA aptamers or multivalent RNA aptamers, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, yeast, mammalian cells, insect cells, plant cells, and the like. The host cell is preferably present either in a cell culture or in a non-human living organism.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to control expression of a target molecule (e.g., a protein or nucleic acid) using an RNA aptamer of the present invention, preferably a multivalent RNA aptamer of the present invention. Transformed cells can be regenerated into whole plants such that the expressed RNA aptamer regulates the function or activity of the target protein in the intact transgenic plants.

In producing transgenic plants, the DNA construct in a vector described above can be microinjected directly into plant cells by use of micropipettes to transfer mechanically the recombinant DNA (Crossway, *Mol. Gen. Genetics*, 202:179–85 (1985), which is hereby incorporated by reference). The genetic material may also be transferred into the plant cell using polyethylene glycol (Krens, et al., *Nature*, 296:72–74 (1982), which is hereby incorporated by reference).

One technique of transforming plants with the DNA molecules in accordance with the present invention is by contacting the tissue of such plants with an inoculum of a bacteria transformed with a vector comprising a DNA molecule or an engineered gene in accordance with the present invention. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHA105) is particularly useful due to its well-known ability to transform plants.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, *Science*, 237:1176–83 (1987), which is hereby incorporated by reference).

After transformation, the transformed plant cells must be regenerated.

Plant regeneration from cultured protoplasts is described in Evans et al., *Handbook of Plant Cell Cultures, Vol. 1*, MacMillan Publishing Co., New York (1983) and Vasil (ed.), *Cell Culture and Somatic Cell Genetics of Plants*, Acad. Press, Orlando, Vol. I (1984) and Vol. III (1986), which are hereby incorporated by reference.

It is known that practically all plants can be regenerated from cultured cells or tissues.

Thus, another aspect of the present invention relates to an engineered gene which includes the DNA sequence encoding a multivalent RNA aptamer, as described above, and a regulatory sequence which controls expression of the DNA sequence encoding the multivalent RNA aptamer.

As described above, one type of regulatory sequence is a promoter located upstream or 5' to the DNA sequence encoding the multivalent RNA aptamer. Depending upon the desired activity, it is possible to select the promoter for not only in vitro production of the multivalent RNA aptamers of the present invention, but also in vivo production in cultured cells or whole organisms, as described above. As shown in FIGS. 1 and 7, the in vivo production can be regulated genetically. Thus, a preferable type of promoter is an inducible promoter which induces transcription of the DNA sequence in response to specific conditions, thereby enabling expression of the multivalent RNA aptamer according to desired therapeutic needs (i.e., expression within specific tissues, or at specific temporal and/or developmental stages).

Preferred promoters for use in the engineered gene of the present invention include a T7 promoter, a hsp70 promoter, a Mtn promoter, a UAShs promoter, and functional fragments thereof. The T7 promoter is a well-defined, short DNA sequence that can be recognized and utilized by T7 RNA polymerase of the bactieriophage T7. The T7 RNA polymerase can be purified in large scale and is commercially available. The transcription reaction with T7 promoter can be conducted in vitro to produce a large amount of the RNA aptamers of the present invention (Milligan et al., "Oligoribonucleotide Synthesis Using T7 RNA Polymerase and Synthetic DNA Templates," *Nucleic Acids Res.* 15(21): 8783–8798 (1987), which is hereby incorporated by reference. The heat shock promoters are heat inducible promoters driven by the RNA polymerase II in eukaryotes. The frequency with which RNA polymerase II transcribes the major heat shock genes can be increased rapidly in minutes over 100-fold upon heat shock. The heat shock promoter used in the present invention is preferably a Drosophila hsp70 promoter, more preferably a portion of the Drosophila hsp70 promoter which is fully functional with regard to heat inducibility and designated heat inducible cassette, or Hic (Kraus et al., "Sex-specific Control of *Drosophila melanogaster* Yolk Protein 1 Gene Expression is Limited to Transcription," *Mol. Cell. Biol.* 8:4756–4764 (1988), which is hereby incorporated by reference). Another inducible promoter driven by RNA polymerase II used in the preferred embodiment of the present invention is a metallothionein promoter, which is inducible to the similar degree as the heat shock promoter in a time course of hours (Stuart et al., "A 12-base-pair Motif that is Repeated Several Times in Metallothionein Gene Promoters Confers Metal Regulation to a Heterologus Gene," *Proc. Natl. Acad. Sci. USA* 81:7318–7322 (1984), which is hereby incorporated by reference). An additional promoter used in the present invention is a constructed hybrid promoter in which the yeast upstream activation sequence for the GAL1 genes was fused to the core Drosophila hsp70 promoter (Brand and Perrimon, "Targeted Gene Expression as a Means of Altering Cell Fates and Generating Dominant Phenotypes," *Development* 118:401–415 (1993), which is hereby incorporated by reference). This promoter is no longer activated by heat shock. Rather, it is activated by the yeast GAL4 protein, a transcription activator that is normally not present in Drosophila. The yeast GAL4 gene has been introduced into Drosophila, and is itself under a variety of transcriptional control in different fly lines.

For example, in vitro production of a pentavalent RNA aptamer from a DNA molecule of the present invention was driven by a T7 promoter. The accurate trimming of the immature RNA transcript at both 5' and 3' ends by the ribozyme allowed the use of a circular template for higher transcriptional efficiency than the conventional run-off transcription (Taira et al., "Construction of a Novel RNA-Transcript Trimming Plasmid Which Can Be Used Both in vitro in Place of Run Off and (G) Free Transcriptions and in vivo as Multi-Sequence Transcription Vectors," *Nucleic Acids Res.* 19:5125–5130 (1991), which is hereby incorporated by reference).

In contrast, in vivo production of the mature pentavalent RNA aptamer was achieved using several different promoters driven by the RNA polymerase II. These promoters are very strong, yet tightly regulated. For example, a BBS dodeca-pentamer transcribed from the promoter of the induced heat shock genes would yield about 1000 B52 binding sites in a minute, which would build up to an intranuclear concentration of more than a hundred nanomolar in about 10 minutes, assuming the half-life of the RNA is significantly longer than this time scale. (The diameter of a Drosophila nucleus is 21 $\mu$m, which results in a nuclear volume of $3.4 \times 10^{12}$. When fully induced, an hsp70 promoter fires productively once every 4 seconds, which follows from the density of RNA polymerase II being one per 80 bp and the elongation rate being 1.2 kb/min.)

In addition, the mature multivalent RNA aptamers can be directed to specific subcellular compartments to ensure that they will encounter the intended target and be concentrated in the organelle where the target resides. To direct in vivo produced RNA to specific subcellular locations, several approaches can be used. RNA will stay in the nuclei if it does not have an exporting signal such as a polyadenyl tail. To export RNA from the nucleus, a specific RNA sequence or structure, such as the Constitutive Transport Element of the type D retrovirus (Bray et al., "A Small Element from the Mason-Pfizer Monkey Virus Genome Makes Human Immunodeficiency Virus Type 1 Expression and Replication Rev-independent," *Proc. Natl. Acad. Sci. USA* 91:1256–1260 (1994); Ernst et al., "A Structured Retroviral RNA Element that Mediates Nucleocytoplasmic Export of Intron-containing RNA," *Mol. Cell. Biol.* 17:135–144(1997), which are hereby incorporated by reference) can be appended to the RNA constructs as ancillary elements. To direct RNA aptamers to other subcellular locations, specific proteins may be attached to the RNA aptamer to carry the RNA to its destiny. A second level of spatial control is achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the RNA aptamers of the present invention, providing a means to restrict the expression of the aptamers in particular tissues.

Additional aspects of in vitro and in vivo production of the mature pentavalent RNA aptamer of the present invention are described in Shi, "Perturbing Protein Function with RNA Aptamers," Thesis, Cornell University, University Microfilms, Inc. (1997), and Shi et al., "Artificial Genes Expressing RNA Aptamers as Specific Protein Inhibitors in vivo," *Nucleic Acids Symp. Ser.* 36:194–196 (1997), which are hereby incorporated by reference.

Another aspect of the present invention relates to a transgenic nonhuman organism whose somatic and germ cell lines contain an engineered gene encoding a multivalent RNA aptamer which inhibits activity of a target molecule to treat a condition associated with an expression level of the target molecule. The engineered gene is a gene of the present invention. The target molecule can be any target used in the selection process, preferably a protein or nucleic acid.

The transgenic non-human organism is preferably a multicellular organism, such as a plant, an animal, or an insect. The plant can be a monocot or a dicot. The animal can be a mammal, an amphibian, a fish, a reptile, or a bird. Preferred transgenic mammals of the present invention include sheep, goats, cows, dogs, cats, all primates, such as monkeys and chimpanzees, and all rodents, such as rats and mice. Preferred insects include all species of Drosophila, particularly *Drosophila melanogaster*.

According to one embodiment of the present invention, the transgenic organism is a transgenic insect, namely *Drosophila melanogaster*, whose somatic and germ cell lines contain an engineered gene encoding a multivalent RNA aptamer which inhibits activity of Drosophila splicing factor B52 to treat various conditions associated with over-expression of Drosophila splicing factor B52.

Related aspects of the present invention involve methods of expressing a multivalent RNA aptamer in a cell which include introducing either a DNA molecule of the present invention or an engineered gene of the present invention into a cell under conditions effective to express the multivalent RNA aptamer. As described above, the conditions under which expression will occur are dependent upon the particular promoter or other regulatory sequences employed.

Another aspect of the present invention relates to a method of inhibiting the activity of a target molecule in a cell which includes expressing a multivalent RNA aptamer in a cell, where the multivalent RNA aptamer has an affinity for the target molecule sufficient to inhibit activity of the target molecule. The target molecule can be any target used in the selection process, preferably a protein or nucleic acid. This method also includes introducing into the cell, prior to the step of expressing, a DNA molecule encoding the multivalent RNA aptamer. As described above, expression of the DNA molecule can be under the control of any one of a variety of regulatory sequences such as promoters, preferably inducible promoters. The cell can be in an in vitro environment, in an in vivo cell culture, or in vivo within an organism.

Another aspect of the present invention relates to a method of increasing activity of a splicing factor protein in a cell. This method includes inserting a multivalent RNA aptamer, which binds to a splicing factor protein, into an RNA transcript, which contains exons and introns, under conditions effective to enable splicing of the RNA transcript. The splicing factor protein is preferably Drosophila splicing factor B52 or a homologous splicing factor. To be effective, the RNA aptamer must be transcribed in cis with the RNA transcript containing the exons and introns. This can be accomplished by inserting a heterologous DNA molecule of the present invention into the genome of a host cell using the techniques described above.

Thus, in trans, the pentavalent RNA aptamer specific for Drosophila splicing factor B52 can suppress the splicing of a pre-mRNA substrate. In cis, the RNA aptamer sequence can enhance B52-dependent pre-mRNA splicing. When the pentavalent RNA aptamer was expressed in vivo, it was efficiently synthesized, it was stable, and it accumulated to high level within the nuclei where its target resides. Moreover, Drosophila splicing factor B52 was demonstrated to be recruited to the chromosome site of production for the pentavalent RNA aptamer, providing direct evidence of their interaction in vivo. The efficacy of the pentavalent RNA aptamer as a Drosophila splicing factor B52 antagonist at the organismal level in Drosophila was demonstrated by its capability of averting all phenotypes caused by B52 over-expression.

Although the use of a plurality of monomeric DNA sequences and a cis-acting ribozyme has been described above in connection with the multivalent RNA aptamer, it should be apparent to one of ordinary skill in the art that this approach is applicable to the expression, in a cell, of any functional RNA molecule, e.g., monovalent or multivalent RNA aptamers, ribozymes, and antisense RNA. Thus, other aspects of the invention include: (1) a constructed DNA molecule that contains a plurality of monomeric sequences each encoding a functional RNA molecule; (2) an engineered gene that includes a DNA sequence that contains a plurality of monomeric sequences each encoding a functional RNA molecule and a regulatory sequence which controls expression of the DNA sequence; (3) methods of expressing a functional RNA molecule in a cell by introducing such a constructed DNA molecule or engineered gene into a cell under conditions effective to express the functional RNA molecule; and (4) a transgenic non-human organism whose somatic and germ cell lines contain an engineered gene that contains a plurality of monomeric sequences each encoding a functional RNA molecule, where the functional RNA molecule encoded by the engineered gene inhibits the activity of a target molecule to treat a condition associated with an expression level of the target molecule.

These aspects of the present invention are further illustrated by the examples below.

EXAMPLES

The following examples are provided to illustrate embodiments of the present invention but they are by no means intended to limit its scope.

The materials and methods described below are applicable for all of the following examples.

Protein Expression and Purification

Target protein from different organisms can be prepared either directly from tissue samples or through recombinant DNA methodology using knowledge in the art. The target in the *Drospohila melanogaster* model system, the full length B52 protein, was expressed in Sf9 cells using the baculovirus expression system. The B52 cDNA used in these Examples was described previously (Kraus and Lis, "The Concentration of B52, an Essential Splicing Factor and Regulator of Splice Site Choice, is Critical for Drosophila Development," *Mol. Cell. Biol.* 14:5360–5370 (1994), which is hereby incorporated by reference) and was cloned into the vector pJVP10Z (Ueda et al., "Human Monocyte Chemoattractant Protein-1 Expressed in a Baculovirus System," *Gene* 140:267–272 (1994), which is hereby incorporated by reference). The transfection, purification, and culturing of the recombinant baculovirus was performed as described previously (Summers and Smith, *A Manual of Methods for Baculovirus Vectors and Insect Cell Culture Procedures*, College Station, Tex., Texas Agricultural Experiment Station (Bulletin No. 1555) (1987); Groebe et al., "Cationic Lipid-Mediated Co-transfection of Insect Cells," *Nucleic Acids Res.* 18:4033 (1990), which are hereby incorporated by reference). The over-expressed B52 was purified using the standard SR protein purification procedure (Zahler et al., "SR Proteins: A Conserved Family of Pre-mRNA Splicing Factors," *Genes Dev.* 6:837–847 (1992), which is hereby incorporated by reference). B52 deletion constructs were generated by PCR amplification of the corresponding regions of the B52 cDNA. They were then cloned into the vector pGEM®-3Z (Promega Corporation, Madison, Wis.). Truncated versions of B52 were made by in vitro translation using the TNT® Coupled Reticulocyte Lysate System (Promega Corporation, Madison, Wis.) with L-($^{35}$S) Methionine (in vivo cell labeling grade, Amersham Life Science Inc., Cleveland, Ohio) according to the manufacturer's instructions. The quality of translation products was checked on SDS-PAGE prior to use.

Oligonucleotides

The template-primer system consists of three oligonucleotides identical or similar to those used by Bartel et al. ("HIV-1 Rev Regulation Involves Recognition of Non-Watson-Crick Base Pairs in Viral RNA," *Cell* 67:529–536 (1991), which is hereby incorporated by reference). The synthesized template, designated Temp, has a nucleotide sequence corresponding to SEQ. ID. No. 15 as follows:

accgagtcca gaagcttgta gtactnnnnn nnnnnnnnnn nnnnnnnnnn nnnnnnnnnn nnnnngccta gatggcagtt gaattctccc tatagtgagt cgtattac 108 where the internal 40 bases is a random sequence. A first primer, designated T7Univ, has a nucleotide sequence corresponding to SEQ. ID. No. 16 as follows:

gtaatacgac tcactatagg gagaattcaa ctgccatcta 40

A second primer, designated RevUniv, has a nucleotide sequence corresponding to SEQ. ID. No. 17 as follows:

accgagtcca gaagcttgta gt 22

These oligonucleotides were synthesized at 0.2 µM quantity by Integrated DNA Technologies, Inc. (Coralville, Iowa).

The templates of the deletion, mutation and antisense constructs of BBS were made as oligonucleotides appended with the T7 promoter sequence. They were synthesized as Gibco BRL Custom Primers.

The monomeric template of the immature pentavalent RNA aptamer was made by ligation of three fragments, each of which was synthesized as a pair of oligonucleotides as Gibco BRL custom primers. Their sequences are as follows:

P1+(SEQ. ID. No. 18)
    accgctcgag agtacgatca accaggcgac agtactctcg acgatcaacc aggcgacagt 60

P1–(SEQ. ID. No. 19)
    aaactgcagt ggcggtcgcc tggttgacca gccactgtcg cctggttgat cgtcgagagt 60

P2+(SEQ. ID. No. 20)
    aaactgcagg gtaacggtca accaggcgac cgttacccgg acggtcaacc aggcg 55

P2–(SEQ. ID. No. 21)
    acgcgtcgac tgaccgaagt caacggtcgc ctggttgacc gtccgggtaa cggtc 55

P3+(SEQ. ID. No. 22)
    accgctcgag atgcatgtcg cggccgcctc cgcggccgcc tgatgagtcc 50

P3–(SEQ. ID. No.23)
    acgcgtcgac atgcatgttt cgtcctcacg gactcatcag gcggccgcgg 50

In vitro Selection

Pool construction: Gel-purified synthetic oligo deoxynucleotides Temp (SEQ. ID. No. 15), T7 Univ (SEQ. ID. No. 16), and RevUniv (SEQ. ID. No. 17) were used as template and primers for a 5-ml PCR reaction carried out in 10 Eppendorf tubes. The temperature cycling was performed by manual transfer among three water baths and stopped after four cycles when the product was still increasing nearly two-fold per cycle. The amplified DNA template was phenol-extracted and ethanol precipitated.

Cycles of selection: RNA for each round was produced using the T7-MEGAshortscript™ in vitro transcription kit for large scale synthesis of short transcript RNAs (Ambion Inc., Austin, Tex.) according to the manufacturer's instructions. Gel purified RNA was quantified by spectrophotometry and diluted into 1×binding buffer (50 mM Tris/Cl, pH 7.6, 200 mM KoAc, 5 mM MgCl$_2$, 2.5 mM dithiothreitol). The pool was heated to 70° C. for 3 minutes and then cooled to ambient temperature over 5 minutes before adding the protein. Prior to every other cycle, the folded RNA pool was also passed through a nitrocellulose filter (HAWP 02500 available from Millipore Inc., New Bedford, Miss.). The binding reaction was performed in 100 µvolume, with 30 µM RNA and 30 nM B52 protein. In the first three cycles, 40 u of rRNasin (Promega Corporation, Madison, Wis.) was also included. The reaction was incubated for 80 minutes, with temperature cycling between 25° C. (or ambient temperature) and 37° C., such that the reaction was at 25° C. for three-quarters of the time (Bartel and Szostak, "Isolation of New Ribozymes From a Large Pool of Random Sequences," *Science* 261:1411–1418 (1993), which is hereby incorporated by reference). Protein-RNA complexes were isolated by filtration and extracted as previously described (Tuerk and Gold, "Systematic Evolution of Ligands by Exponential Enrichment: RNA Ligands to Bacteriophage T4 DNA Polymerase," *Science* 249:505–510 (1990), which is hereby incorporated by reference). The selected RNAs were amplified using the SUPERSCRIPT™ Pre-amplification System for First Strand cDNA Synthesis and Taq DNA Polymerase (Life Technologies Corporation, Gaithersburg, MD) according to the manufacturer's instructions.

Cloning and Sequencing

The pool DNAs were cloned in the vector pGEM®-3Z, between the EcoRi and HindIII sites of the poly-linker region. Individual clones were sequenced using the Taq cycle sequencing method with DyeDeoxy™ Terminators on a Applied Biosystems 737A automated DNA Sequencer by the DNA Services facility at Cornell Biotechnology Programs.

RNA-Protein Binding Assay

The RNA probes were uniformly labeled with [a-$^{32}$P] UTP (Amersham Life Science Inc., Cleveland, Ohio) using the T7-MAXIscript™ in vitro transcription kit (Ambion, Inc., Austin, Tex.) according to the manufacturer's instructions. When the cloned sequences from the selected pools were to be used, the plasmids were linearized by digestion with ScaI to serve as templates. The templates of the deletion, mutation, and antisense constructs of BBS were made as oligonucleotides appended with the T7 promoter sequence. They were synthesized as GibcoRBL Custom Primers. The template plasmids of the immature pentavalent RNA aptamer were linearized by digestion with EcoRI. The RNAs used as competitors were prepared using the T7-MAGAshortscript™ in vitro transcription kit (Ambion, Inc., Austin, Tex.) according to the manufacturer's instructions. Prior to use in a binding assay, the majority of transcripts of each RNA preparation were shown to be of the expected size by electrophoresis on an 8% polyacrylamide, 7 M urea gel.

All binding assays were performed in 20 $\mu$l volume in 1×binding buffer described above. A typical binding assay using labeled RNA contains about 20 fmole of $^{32}$P-labeled RNA probe and differing amounts (1–10 pmole) of B52 protein. A typical binding assay using the truncated versions of B52 contains 1 $\mu$l of the $^{35}$S-labeled translation reaction mixture with 2 pmoles of unlabeled RNA transcript (the final concentration of RNAs in this reaction was 100 nM and concentration of the labeled B52 proteins was much lower). The reactions were allowed to equilibrate for 15–20 minutes at ambient temperature before being subjected to filter binding, gel shift, or UV crosslinking.

Gel shifts were performed at 4° C. The binding reaction mixtures were set at 4° C. for 5–10 minutes before being loaded onto a 2.5% agarose gel in 1/4 TBE buffer. The avidity of the pentavalent RNA aptamer to B52 was examined on longer agarose gels (25 cm) to improve the resolution of RNA bands. The affinity of the RNA for the in vitro translated polypeptides was estimated by comparing the intensity of the bands representing the complex on the agarose gel and that of the corresponding polypeptides run on SDS-PAGE. To crosslink proteins to RNA, the binding reaction mixtures were irradiated for 20 minutes from 5 cm directly above by inverting a short-wavelength UV transilluminator. The products of crosslinking were analyzed using standard SDS-PAGE.

Footprinting

Footprinting procedures were modified from those previously reported (Christiansen et al., "Analysis of rRNA Structure: Experimental and Theoretical Considerations" in *Ribosomes and Protein Synthesis: A Practical Approach*, Spedding (ed.), IRL Press, New York (1990), which is hereby incorporated by reference). The RNA substrate (100 ng) was incubated with or without B52 under binding conditions. RNase T2 (1u) or RNase V1 (0.35u) was added and incubated at room temperature for 1 minute. The digestion was stopped by a phenol and chloroform extraction followed by ethanol precipitation. The precipitated RNAs were re-suspended and analyzed by primer extension with $^{32}$P labeled pUC/M13 reverse sequencing primer and Superscript II Reverse Transcriptase (Life Technologies) and then separated on either a 6% (RNase T2 digestion) or 8% (RNase V1 digestion) sequencing gel.

Splicing Assay

The inhibitory RNA was prepared in vitro with the T7-MAGAshort script™ in vitro transcription kit (Ambion, Inc., Austin, Tex.) and purified on a 5% polyacrylamide gel with 7M urea. The ftz pre-niRNA was produced by run-off transcription from XhoI linearized plasmid pGEM2 V61 SIB (Rio, "Accurate and Efficient pre-mRNA Splicing in Drosophila Cell-free Extracts," *Proc. Natl. Acad. Sci. USA* 89:2904–2908 (1998), which is hereby incorporated by reference). The pentavalent monomeric unit of BBS, P1-2-3/BBS(5), was cloned into the same XhoI site of the pGEM V61 S/B in both directions, resulting in the plasmids V61+ 1×5 (ftz+BBS(5)) and V61-1×5 (ftz-BBS(5)). When used as templates, V61+1×5 was linearized by NotI, and V61-1×5 by ScaI. Nuclear and cytoplasmic (S100) extracts were made from Kc cells (Dignam et al., "Accurate Transcription Initiation by RNA Polymerase II in a Soluble Extract from Isolated Mammalian Nuclei," *Nucleic Acids Res.* 11:1475–1489 (1983), which is hereby incorporated by reference). In vitro splicing reactions were assembled essentially as described in Rio, "Accurate and Efficient Pre-mRNA Splicing in Drosophila Cell-free Extracts," *Proc. Natl. Acad. Sci. USA* 89:2904–2908 (1988), which is hereby incorporated by reference, and carried out at 20° C. for 90 minutes. The resulting RNAs were separated on a 6% polyacrylamide gel containing 7M urea.

RNase Protection Assay

Total RNA from transfected cells was prepared with Trizol reagent (Life Technologies Corporation, Gaithersburg, MD). Total RNA from flies was prepared using the RNAqueous Total RNA Isolation Kit (Ambion Inc., Austin, Tex.) from late third instar larvae. RNase protection assay was performed using the HybSpeed RPA protocol (Ambion Inc., Austin, Tex.). To determine the abundance of the pentavalent RNA aptamer, the internally labeled antisense transcript of part of the monomeric pentavalent RNA aptamer sequence was used as probe. 4 $\mu$g of the RNA samples from transfected cells or 1–2 μg of RNA samples from larvae, both DNase treated, were used in each assay.

Cell transfection

To construct the HicBBS series and the MtnBBS series of plasmid, the transcriptional templates of the immature pentavalent RNA aptamer were lifted from the pSP73 vectors as XhoI-SalI fragments and cloned into the SalII site of Hic-L vector (Kraus et al., "Sex-Specific Control of *Drosophila melanogaster* Yolk Protein 1 Gene Expression is Limited to Transcription," *Mol. Cell. Biol.* 8:4756–4764 (1988), which is hereby incorporated by reference) or the XhoI site of pMtnEX vector. Both orientations of the insert were recovered in some cases. 2.5 μg plasmid DNA was used to transform each 6 mm plate of S2 cells (initially 5×10$^6$) with Lipofectin (Life Technologies Corporation, Gaithersburg, Md.) according to the manufacturer's instruction. The genes were induced 24 hours after transfection by either heat shock at 36.5° C. for 90 minutes or adding $CuSO_4$ to final concentration of 0.5 mM for 24 hours. The half life of the mature pentavalent RNA aptamer was measured by treating the cells with actinomycin (Life Technologies, 35 μl, 1 mg/ml) immediately after heat shock, and harvesting cells at 0, 2, 4, and 8 hours thereafter.

Generation of Transgenic Fly Lines

The gene encoding the mature pentavalent RNA aptamer was moved from the HicBBS(5.12) plasmid as a BamHI-EcoRV fragment to the BamHI-HpaI site of the pW8 vector (Klemenz et al., "The White Gene as a Marker in a New P-Element Vector for Gene Transfer in Drosophila," *Nucleic Acid Res.* 15:3947–3959 (1987), which is hereby incorporated by reference) to generate the pW8-HicBBS (5.12) plasmid. To generate the pUASBBS series of plasmids, the different length transcriptional templates (i.e., dimers, tetramers, octamers, or dodecamers) of the pentavalent RNA aptamer, as XhoI-SalI fragments, were cloned into the XhoI site of the pUAST vector (Brand and Perrimon, "Targeted Gene Expression as a Means of Altering Cell Fates and Generating Dominant Phenotypes," *Development* 118:401–415 (1993), which is hereby incorporated by reference). Drosophila germ line transformation was performed according to a previously developed protocol (Park and Lim, "A Microinjection Technique for Ethanol-Treated Eggs and a Mating Scheme for Detection of Germ Line Transformants," *Dro. Inf. Serv.* 76:197–199 (1995), which is hereby incorporated by reference) with minor modifications. Briefly, the embryos from w, Δ2–3 (99B) were collected from orange juice collection plates and immersed in 95% ethanol for 3.5 minutes before being arranged on an orange agar coated coverslip. The DNA preparation was injected at concentration of 500 ng/μl. The coverslip was put on a grape plate and kept at room temperature. The flies recovered were mated individually with $z^1W^{11e4}$ to establish two or three broods and all progeny were examined for colored eyes. Independent transformants were back crossed to $z^1w^{11e4}$ several times to generate stable lines before homozygosing. At least two independent transformants were isolated for each construct.

Figure 14:
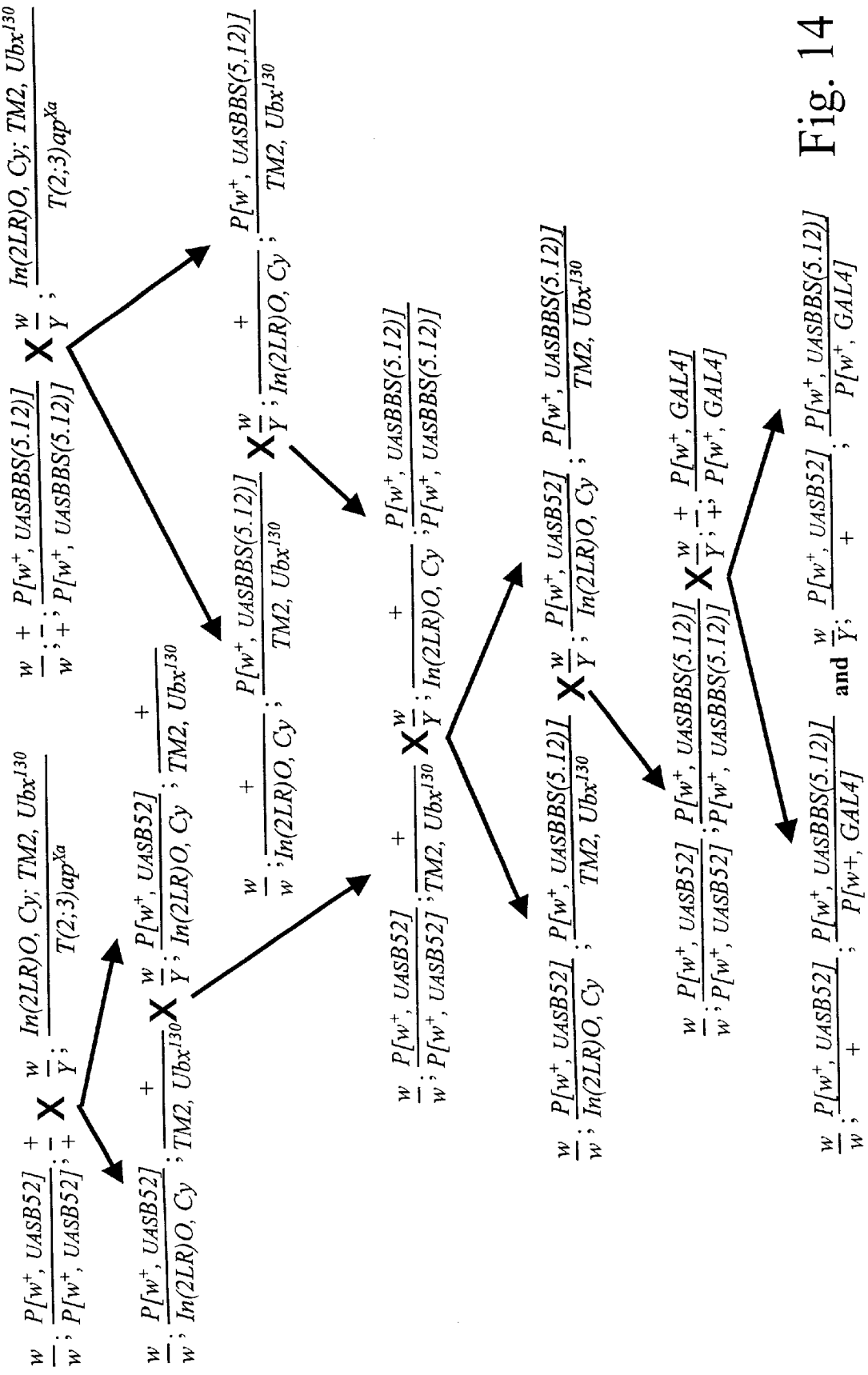
FIG. 14 is a schematic illustration of crosses for synthesizing triple transgenic fly lines by manipulating chromosomes two and three. The scheme shown here illustrates the synthesis of a UASB52 transgene on the second chromosome and a UASBBS(5.12) transgene on the third chromosome to make a homozygous double transgenic line UASB52-UASBBS, which is then mated with a homozygous GAL4 line to generate the heterozygous triple transgenic flies in which both B52 and BBS are actively transcribed. An additional strain is used in the scheme to mark and balance these two chromosomes. Synthesized double transgenic lines are maintained either as homozygous or double balanced stocks.

To express the UASBBS genes, a number of GAL4 lines were mated with different UASBBS lines. To generate the triple transgenic flies containing the B52, BBS, and GAL4 transgenes, one representative transgene from each suite of GAL4, UASB52, and UASBBS transgenes was first selected to synthesize three double transgenic fly lines, UASB52-UASBBS, hsGAL4-UASB52, and hsGAL4-UASBBS. The double transgenic fly lines were synthesized by manipulating the second and the third chromosome with an additional multiple balancer line, CUX, whose genotype is In(2 LR)O, Cy; TM2, $Ubx^{130}/T(2;3)ap^{Xa}$. Each of the double transgenic lines was then mated with a series of corresponding single transgenic lines to produce heterozygous triple transgenic flies. A scheme is shown in FIG. 14 that illustrates the synthesis of an UASB52 transgene on the second chromosome and an UASBBS(5.12) transgene on the third chromosome to make a homozygous double transgenic line UASB52-UASBBS, which is then mated with a homozygous GAL4 line to generate the heterozygous triple transgenic flies in which both B52 and BBS are actively transcribed. All transgene-bearing chromosomes were kept homozygous, except those in the hsGAL4-UASB52, which were balanced. All fly lines were maintained at 24° C. For heat shock treatment, flies in glass vials were kept in a 36.5° C. incubator for the indicated time. In most cases, reciprocal crosses of each genotype was set up by mating 5 females with 3 males in a glass vial. Larval phenotype were examined at the 6th day after mating; surviving adults were examined and counted at 16th day.

In situ Hybridization and Immunofluorescence

The RNA probe was internally labeled with ChromaTide Texas Red-5-UTP (Molecular Probes, Inc., Eugene, OR) by in vitro transcription with T7 RNA polymerase. Hybridization of the probe to whole, formaldehyde-fixed salivary gland tissue was performed at 60° C. overnight in solution containing 50% formamide, 5×SSC, 100 μg/ml yeast RNA, 50 μg/ml heparin, and 0.1% Tween-20. The glands were subsequently washed at 60° C. for 3–4 hours in eight changes of solution in which the hybridization buffer is gradually displaced by the PBT buffer (Drosophila PBS plus 0.1% Tween-20). Polytene chromosome spreads were prepared from salivary glands of late third instar larvae according to (Champlin et al., "Distribution of B52 Within a Chromosomal Locus Depends on the Level of Transcription," *Molec. Biol. Cell.* 5:71–79 (1991), which is hereby incorporated by reference) with minor modification.

The anti-B52 antibody was described in (Kraus and Lis, "The Concentration of B52, an Essential Splicing Factor and Regulator of Splice Site Choice, is Critical for Drosophila Development," *Mol. Cell. Biol.* 14:5360–5370 (1994), which is hereby incorporated by reference). Immunofluorescence was performed as described in (Champlin et al., "Distribution of B52 Within a Chromosomal Locus Depends on the Level of Transcription," *Molec. Biol. Cell.* 5:71–79 (1991), which is hereby incorporated by reference).

Example 1

Identification of B52 Aptamers

The B52 target protein used in the selection was overexpressed from a baculovirus construct in insect cells. The B52 produced by these insect cells appears to be full length and properly modified, as it has the same electrophoretic mobility as the Drosophila protein. Immunoblot analysis of this same preparation using a B52 specific antibody displays the identical mobility of B52 when produced in baculovirus or assayed in Drosophila nuclear extract. In addition, baculovirus produced B52 is fully active in an in vitro splicing assay. Truncated versions of B52 were not used as target because the involvement of the SR domain in possible sequence-specific binding could not be excluded a priori.

The pool of random RNA was carried through nine rounds of selection and amplification. RNA-protein complexes were selected by binding to nitrocellulose filters. A significant increase in affinity by the pool for B52 was observed as the selection progressed. Fractions of two final pools were cloned and sequenced. Some cloned sequences were found in duplicate or triplicate, indicating that the complexity of these selected pools was quite low.

Figure 2B:
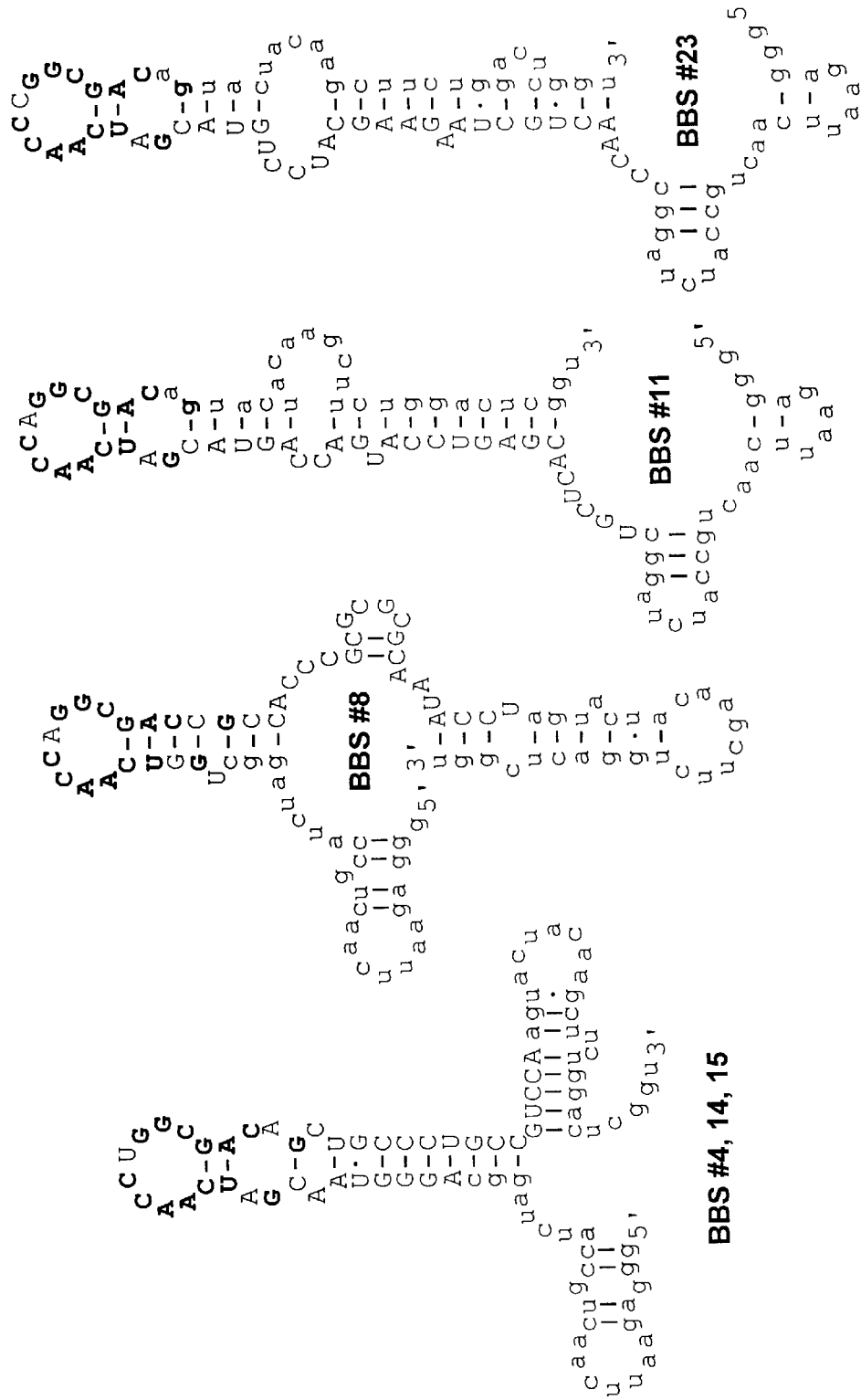

The B52 aptamer family in the selected pools consists of four different sequences, one of which occurred in three separate isolates (FIG. 2). Since all six members of this family showed specific binding to B52, they are designated as a B52-Binding Sequence or Site ("BBS").

As previously described, BBS #4,14,15 has a nucleotide sequence corresponding to SEQ. ID. No. 1, BBS #8 has a nucleotide sequence corresponding to SEQ. ID. No. 2, BBS #11 has a nucleotide sequence corresponding to SEQ. ID. No. 3, and BBS #23 has a nucleotide sequence corresponding to SEQ. ID. No. 4.

These sequences have a conserved region (SEQ. ID. No. 5) which contains two absolutely conserved hexamers separated by a variable nucleotide. There is also a conserved G in the flanking region of either side one base from the end of the double-hexamer. This sequence motif is found in different sequence contexts and in different positions of the randomized region. In two of these sequences, BBS #8 (SEQ. ID. No. 2) and BBS #4/14/15 (SEQ. ID. No. 1), sequence similarity extends further downstream, covering a region of additional 16 nucleotides in length.

The computer program MulFold (Jaeger et al., "Improved Predictions of Secondary Structures for RNA," *Proc. Natl. Acad. Sci. USA* 86:7706–7710 (1989); Zuker, "On Finding All Suboptimal Foldings of an RNA Molecule," *Science* 244:48–52 (1989), which are hereby incorporated by reference) was utilized to examine the free energy minimized secondary structures of the BBS's with their flanking constant region (i.e., the RNA molecules as they were selected). The conserved region of all four different sequences was predicted to fold into a common secondary structure element core (FIG. 3B): the double-hexamer forms the loop portion and part of the stem portion of a hairpin loop structure, and its flanking regions form the extended stem which may contain a bulge or internal loops. In different structures, the hairpin loop encompasses from 23 to 38 nucleotides with 6 to 12 Watson-Crick base pairs and some G-U pairs. The loops and the top of the stems are identical in all four structures, with the loop portion containing nucleotides 5–12 of SEQ. ID. No. 5. Since the random sequence was only 40 nucleotides in length, it is not surprising that this structural element includes sequences from the primer annealing region in some cases. Some bases in the constant region on either side of the random stretch even become part of the conserved sequence of different BBS's. These structures suggest that the common structural element may be selected for binding to B52.

When individual RNA's transcribed from cloned sequences were tested by filter binding assay the BBS RNA's were all able to bind B52 to generate signals that were 20 times the background produced by RNA's from the unselected pools. A band shift assay was also developed as an independent way to assess the affinity and specificity of binding of the selected sequences to B52, and these results are shown in FIGS. 3A and 3B. After cloning the selected sequences, RNA transcripts without most of the 3' constant region were made by cutting the template with the restriction endonuclease ScaI. For BBS #8 (SEQ. ID. No. 2) and BBS #14 (SEQ. ID. No. 1) this trimming did not interfere with stem formation. The band shift assay was first performed with these sequences. Two sequences randomly picked from the original unselected pool were used as controls. Increasing amounts of B52 were added to $^{32}$P-labeled RNA probes, which contain the 5' constant region, in the presence of a large excess of tRNA. Stable complexes were formed with BBS sequences but not with the control sequence from the unselected pool. Since only one shifted complex is observed, and B52 is a monomer, it could be assumed the interaction between B52 and RNA has a 1:1 stoichiometry. Because the concentration of the RNA probes in these reactions is negligible as compared to that of B52, the apparent dissociation constant of the complex was estimated to be roughly equal to the protein concentration at which 50% RNA is bound. For example, lane 6 of FIG. 3A, where 50% of RNA is bound, indicates that the $K_d$ of the B52-BBS #14 (SEQ. ID. No. 1) complex is about 50 nM. BBS #8 (SEQ. ID. No. 2), also on this gel, displayed an even higher affinity to B52, with a $K_d$ of approximately 20 nM.

The specificity of the B52-RNA interaction was examined by subjecting it to the challenge of different specific competitors. As shown in FIG. 3B, a constant amount of B52 (5 pmole) was incubated with increasing amounts of three different unlabeled RNA competitors before the addition of either the BBS #8 (SEQ. ID. No. 2) or BBS #14 (SEQ. ID. No. 1) probes. It is obvious that both BBS #8 (SEQ. ID. No. 2) and BBS #14 (SEQ. ID. No. 1) can compete with themselves (Lanes 1–3 & 13–15), and with each other (Lanes 4–6 & 10–12), but the random control sequence, designated G0, does not compete with these interactions (Lanes 7–9 & 16–18). G0 has a nucleotide sequence corresponding to SEQ. ID. No. 24 as follows:

gagacccacc gacacctcgg ccggcggggc ttttagcgag 40

To further test the specificity of the BBS, additional binding assays were performed. RBP 1, another Drosophila SR protein, and HSF, the Drosophila heat shock factor did not show any measurable affinity for the BBS RNA's. Also, since B52 has been shown previously to crosslink with DNA in vivo (Champlin et al., "Distribution of B52 Within a Chromosomal Locus Depends on the Level of Transcription," *Molec. Biol. Cell.* 5:71–79 (1991), which is hereby incorporated by reference), single-stranded DNA containing the BBS motif was also tested for its ability to bind B52. No B52-DNA complex was detected in the band shifting assay under similar conditions used for BBS RNA transcripts. These results indicate that B52 possesses distinct RNA binding specificity for the BBS RNA.

Example 2

Defining the Minimum RNA Sequence Requirements for Binding to B52

To determine the sequence/structure requirements for binding by B52, deletion and substitution mutations, and antisense constructs of BBS were designed in light of the shared sequence motif and predicted secondary structures (FIG. 4). These short RNA transcripts were produced by in vitro transcription of synthetic templates, and their affinity to B52 was assayed by band shift.

The approximate 5' and 3' termini of the aptamer binding site were determined by deletion analysis. Based on the sequence of BBS #8 (SEQ. ID. No. 2), an RNA construct, BBS-I/Long, was made to contain the region shared by all BBS RNAs plus the region only shared with #14, but missing both 5' and 3' constant regions. The nucleotide sequence of BBS-I/Long (SEQ. ID. No. 25) is as follows:

ggcuggucaa ccaggcgacc gccacccgcg cgc 33

It was predicted to retain the BBS #8 hairpin loop structure, which is the shortest and most stable hairpin among the four BBS's, plus a 3' unfolded tail. This construct demonstrated full binding activity.

Next, the 3' tail was deleted to make the construct BBS-I, which contained only the hairpin loop structure; it was also fully active. The nucleotide sequence of BBS-I (SEQ. ID. No. 26) is as follows:

ggcuggucaa ccaggcgacc gcc 23

A third deletion construct, designated BBS-I/NoBulge, was prepared by deleting the bulged U in the stem. Its binding activity was not compromised either. The nucleotide sequence of BBS-I/NoBulge (SEQ. ID. No. 27) is as follows:

ggcggucaac caggcgaccg cc 22

Another construct, designated BBS-II, which is part of the BBS #11 sequence (SEQ. ID. No. 3) and has the conserved hairpin loop with an internal loop in the stem, binds B52 as well as BBS-I. The nucleotide sequence of BBS-II (SEQ. ID. No. 28) is as follows:

ggguacgauc aaccaggcga caguaccc 28

However, when several nucleotides on each side of BBS-II were deleted to decrease the stability of the stem, the affinity to B52 decreased almost by a factor of three. This construct, designated bbs-II, was comparable to BBS-I in length, containing the sequence shared by all members of BBS family, and was predicted to have no stable secondary structure in solution. However, the possibility that non-Watson-Crick base pairs, base-ribose, and/or base-phosphate interactions may occur in the internal loop region to produce a compact and stable structure, or that binding to B52 may stabilize the remaining weak pairs to give a structure like the one in the full sequences cannot be ruled out. The nucleotide sequence of bbs-II (SEQ. ID. No. 29) is as follows:

ggacgaucaa ccaggcgaca gu 22

The last deletion construct, designated AltStem, contained only the double-hexamer region plus one of the two conserved G's at the 5' end. The resulting predicted structure, a smaller and slightly different hairpin, still retained some low affinity for B52, but much less than that of bbs-II. The sequence of AltStem (SEQ. ID. No. 30) is as follows:

ggucaaccag gcgac 15

The above data suggest that both primary sequence and secondary structure of the RNA's contribute to their affinity for B52. Therefore, substitution variants were prepared to separate the effect of sequence and structure. Based on the sequence of BBS-II (SEQ. ID. No. 28), the variant FlipBBS-II was prepared by interchanging part of the sequences in each half of the stem. The nucleotide sequence of FlipBBS-II (SEQ. ID. No. 31) is as follows:

ggcaugaauc aaccaggcga cgcaugcc 28

Based on the sequence of BBS-I (SEQ. ID. No. 26), the variant TransBBS-I was prepared by making two G-C to A-U transitions in the stem. Both these constructs, in which the conserved flanking G's were replaced, exhibited poor binding even though their predicted secondary structures were unaffected by the changes. The nucleotide sequence of TransBBS-I (SEQ. ID. No. 32) is as follows:

ggaugucaac caggcgacau cc 22

Then based on bbs-II, the unstable internal loop region was converted into a stem by changing sequences on either side of the loop, resulting in the variants bbs-II/5'Stem and bbs-II/3'Stem, respectively. The nucleotide sequence of bbs-II/5'Stem (SEQ. ID. No. 33) is as follows:

ggacugucaa ccaggcgaca gu 22

The nucleotide sequence of bbs-II/3'Stem (SEQ. ID. No. 34) is as follows:

ggacggucaa ccaggcgacc gu 22

Although both have a similarly stable hairpin loop structure, bbs-II/5'Stem, which has only one conserved flanking G, was a weak binder, while bbs-II/3'Stem, which has both conserved flanking G's, was a strong one. In making bbs-II/3'Stem, a sequence identical to that of BBS-I was generated in between the two end-most conserved G's.

As a negative control, antisense RNA of BBS-I and bbs-II were made.

The nucleotide sequence of Antibbs-1 (SEQ. ID. No. 35) is as follows:

ggcggucgcc ugguugacca gcc 23

The nucleotide sequence of AntiBBS-II (SEQ. ID. No. 36) is as follows:

ggacugucgc cugguugauc gu 22

Both antisense constructs did not bind B52, although AntiBBS-I (SEQ. ID. No. 35) has a hairpin loop structure similar to BBS-I.

In addition, the importance of the single-strandedness of the core BBS consensus was assessed by linking it to its antisense sequence via a UUCG tetra-loop.

The nucleotide sequence of UUCG/BBS (SEQ. ID. No. 37) is as follows:

ggucgccugg uugaucuucg gaucaaccag gcgaca 36

The BBS consensus sequence trapped in an RNA duplex lost its binding activity.

These experiments demonstrated that the sequence between and including the two end-most conserved G's (i.e., SEQ. ID. No. 5) is required for efficient recognition by B52. While most of the conserved sequence resides in the loop, these variants showed that particular sequences of the stem, particularly the conserved flanking G's, are also critical for this interaction. The flanking region on both sides of this conserved sequence segment can contribute to binding. While not wishing to be bound by a particular theory, it is believed that the flanking regions help to form a more stable stem, probably by pre-paying some entropic cost of the interaction.

On the basis of the binding results, it was determined that a strong B52-binding site on RNA contains at least 17 nucleotides, namely SEQ. ID. No. 5, and generally about 20 nucleotides, which is the length of most hairpin loops tested.

Example 3

Probing the Secondary Structure and Critical Regions in the B52-Binding Site of RNA To delineate at higher resolution the B52 binding region on the selected RNA, RNase footprinting was performed with the cloned BBS #8 (SEQ. ID. No. 2). Two RNases with different specificities were used to determine the region of binding in both single and double stranded areas of RNA. These experiments have the added benefit of confirming the predicted hairpin loop secondary structure of the selected RNA.

RNase T2 is a single-strand specific endoribonuclease with low specificity (a preference for adenines), while RNase V1 cleaves RNA predominantly at double-stranded regions with no apparent sequence specificity. Both free RNA and RNA-B52 mixtures were treated with RNase T2 and V1, and the resulting RNA products were detected by primer extension. This allowed an accurate identification of the protected nucleotides, since sequencing reactions using the same primer could be run alongside of the footprinting reactions. A comparison of the primer extension products from free RNA with those from RNA-B52 mixtures identified residues that are in contact with the protein. As the B52 concentration is increased, the intensity of several bands decreased (FIG. 3A, Lanes 2–3 and 9–11). Comparing the position of these bands directly to the sequencing ladder served to identify bases that are protected by the binding of B52. These B52-protected bases reside in the predicted hairpin loop region (FIG. 3B). In addition, the cleavage of the RNA substrate by these RNases in the absence of B52 confirms the predicted hairpin loop secondary structure of the selected RNA. The RNase protection results provide physical evidence that the conserved hairpin loop of BBS RNA is the target of B52 interaction.

Example 4

Locating the RNA-binding Site of B52 to Both RRMs

BBS RNAs were selected for their ability to bind full length B52 protein. It is possible that B52 binds RNA through either one or the other RRMs, the SR domain, or a combination of these domains. To identify the specific RNA-binding site on B52, a set of $^{35}$S-methionine labeled B52 deletion constructs were prepared by in vitro translation and then tested for their ability to bind the selected BBS #8 RNA in two different assays (FIG. 3A). These polypeptides also serve as a second source of target proteins in binding assays to confirm the specificity of binding to the selected BBS RNA.

Figure 6A:
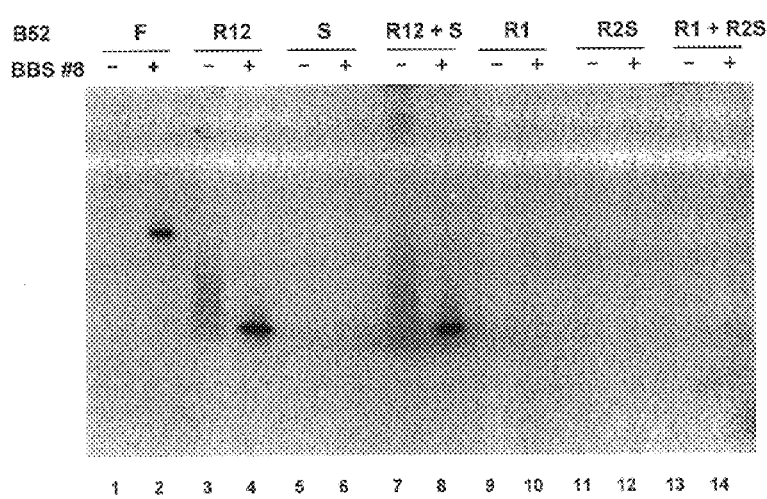
FIGS. 6A and 6B contain images which indicate that the RNA-binding site on B52 was localized to both RNA recognition motifs. $^{35}$S-Methionine labeled B52 deletion constructs were made by in vitro translation, and their ability to bind BBS #8 RNA was examined in two different assays. The binding reactions with different $^{35}$S-labeled proteins or combinations thereof were followed by band shift assay on a native agarose gel, shown in FIG. 6A, or UV crosslinking and SDS-PAGE, shown in FIG. 6B. The filled arrowhead in FIG. 6B signifies the B52/R12-BBS #8 complex, whereas the open arrow head points to where the B52/R1-BBS #8 complex would be expected to migrate. F=full length B52, R1=RRM 1, R2=RRM 2, R12=RRM 1 and RRM2, and S=SR domain.

The in vitro translated polypeptides were examined on SDS-PAGE to verify that they were of the predicted size before being used in the binding assays. The integrity of two polypeptides, R1 and R12, is shown in FIG. 3B. Other polypeptides were made in an identical way and had similar quality. FIG. 3A shows a band shift assay with individual $^{35}$S-labeled polypeptides or these in combination. The binding reaction was set up as previously described, but with a constant amount of BBS #8 RNA transcript in molar excess relative to protein. In the presence of BBS #8 RNA, $^{35}$S-labeled full length B52, F, showed a discrete band (Lane 2, FIG. 3A), which has the same mobility as that of a B52-BBS #8 complex generated with $^{32}$P labeled RNA. The polypeptide containing both RRMs, R12, gave rise to a band running faster than the full length B52-BBS #8 complex (Lane 4, FIG. 3A). The SR domain (S, Lane 6, FIG. 3A), the RRM I (R1, Lane 10, FIG. 3A), and a polypeptide containing both the RRM II and the SR domain (R2S, Lane 12, FIG. 6A) did not produce any discrete band on this native gel. When the polypeptides containing the two RRMs (R12) and the SR domain (S) were put together in the presence of the RNA, a band (Lane 8, FIG. 6A) was observed with similar mobility as that seen with R12 in Lane 4. No shifted band was produced with the other combination, polypeptides R1 plus R2S. These data indicate that the SR domain of B52 does not participate in any interaction with an RNA aptamer, and both RRMs are required for the binding. In addition, the affinity of the RNA for both in vitro synthesized polypeptides F and R12 is comparable to that measured previously using baculovirus produced B52 protein in excess over RNA.

Figure 6B:
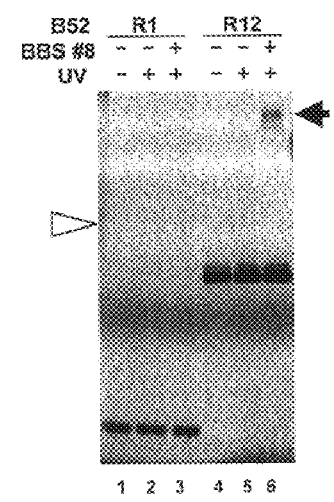
Figure 8A:
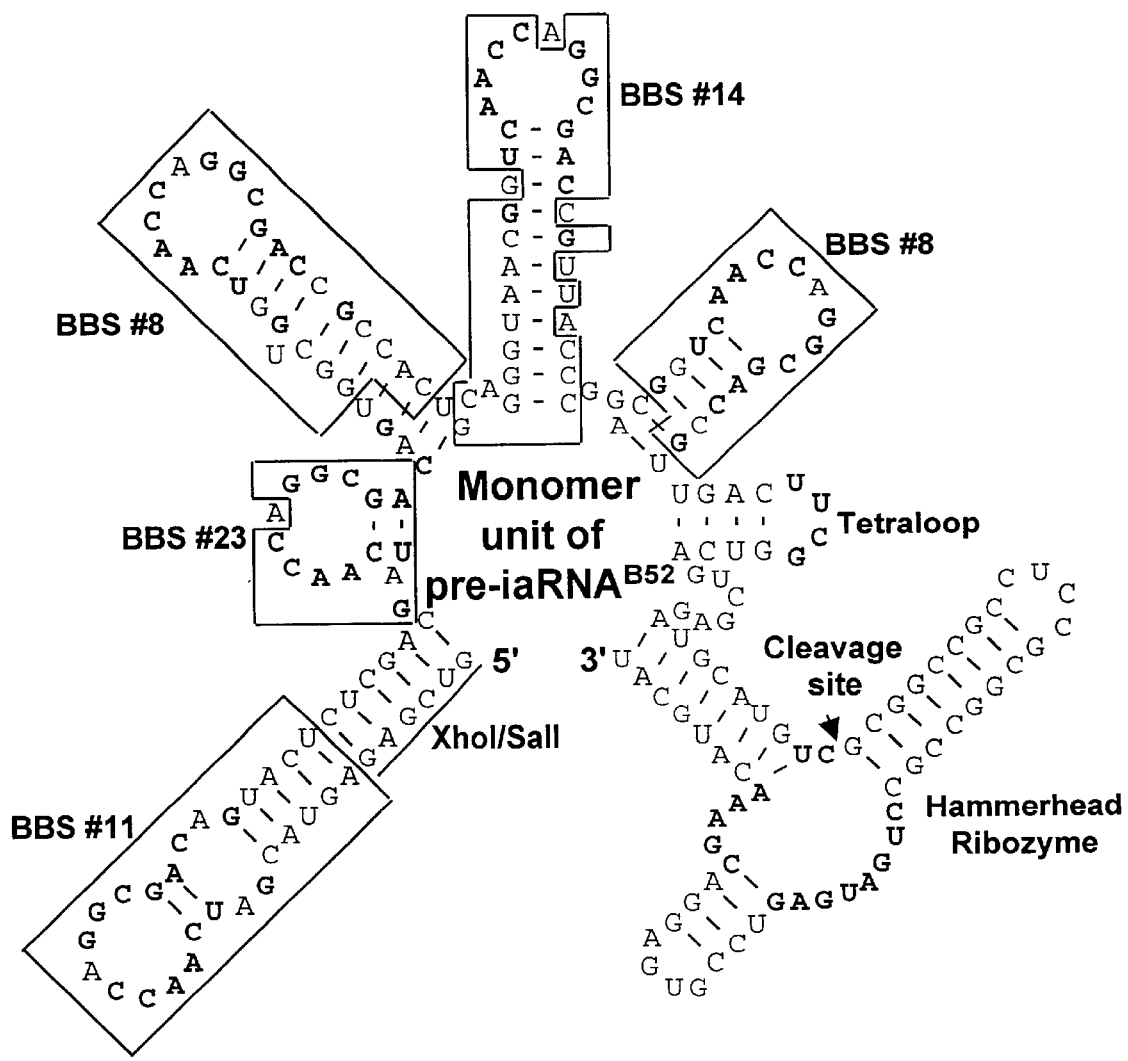
FIGS. 8A and 8B illustrate predicted secondary structures for a multivalent RNA aptamer of the present invention. In particular.
Figure 8B:
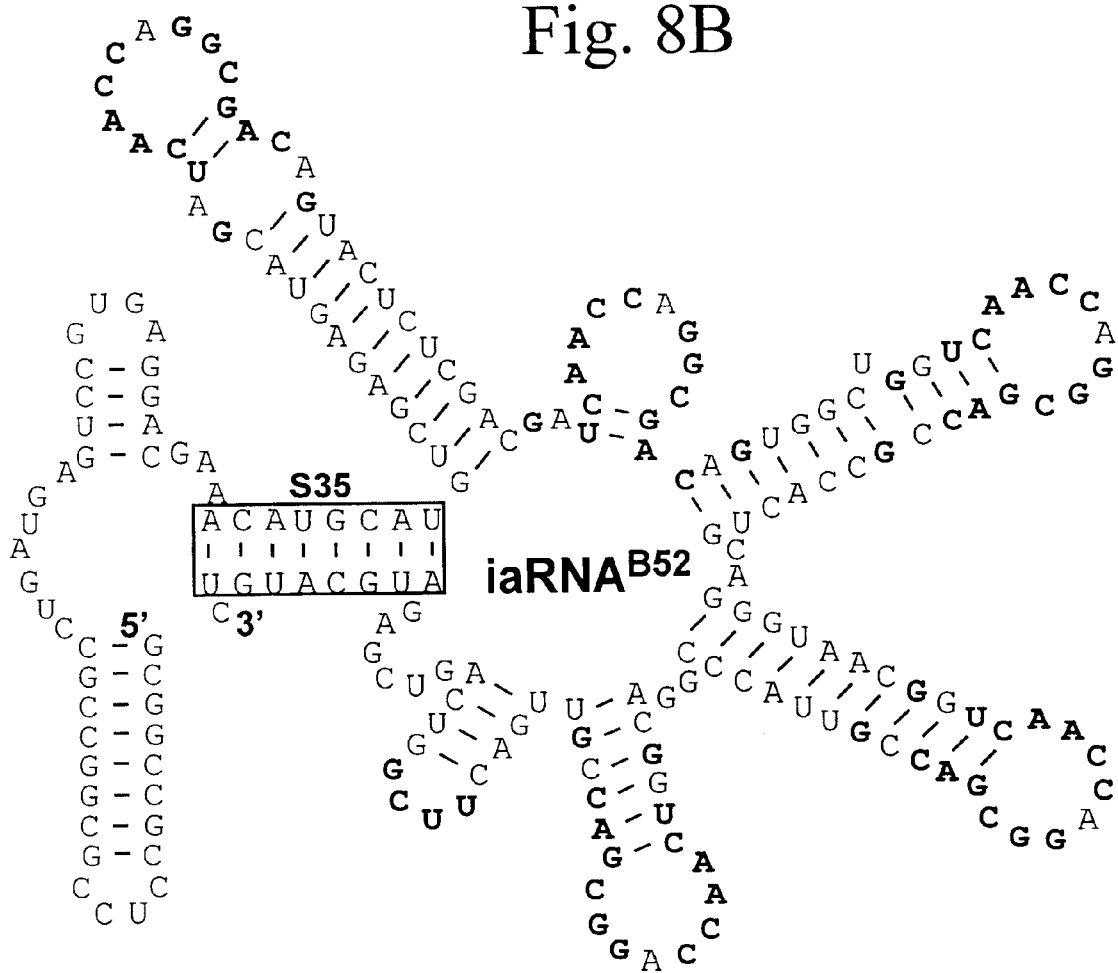

To confirm the requirements of both RRMs for binding, these binding reactions were repeated and the reaction mixtures were subjected to UV irradiation. The UV-crosslinked species were then analyzed on SDS-PAGE. As shown in FIG. 6B, R12 can be crosslinked to the BBS #8 RNA, forming a complex with its apparent molecular weight being the sum of the protein and RNA components (Lane 6). In contrast, Ri was not crosslinked to RNA (Lane 3, FIG. 6B). In these reactions, equal molar amounts of protein were used. Besides, both RRMs must be in cis to bind RNA, since R2S cannot complement RI to restore the binding even when the RNA is at much a higher concentration.

Example 5

Construction of the DNA Molecule Encoding the Pentavalent RNA$^{B52}$ Aptamer Specific for Drosophila and its Expression System The monomeric template of the pentavalent RNA aptamer was made as 20 three pairs of synthetic oligonucleotides. Each pair was annealed and digested with proper restriction endonucleases to generate compatible sticky ends (PstI, XhoI or SalI). The three fragments were ligated to form the monomer template P1-2-3/BBS(5. 1), which was cloned in between the XhoI and SalI sites of the pSP73 vector (Promega Corporation, Madison, Wis.). After its sequence was confirmed, the monomer unit was prepared in large scale as the XhoI-SalI fragment, and ligated into polymers in the presence of both restriction enzymes in standard ligation buffer at DNA concentrations of 100–200 ng/μl (Xiao and Lis, "A Consensus Sequence Polymer Inhibits in vivo Expression of Heat Shock Genes," Mol. Cell. Biol. 6:3200–3206 (1986), which is hereby incorporated by reference) to produce a head-to-tail array of the XhoI-SalI fragments that are resistant to both restriction enzymes. Polymers of different length (e.g., dimers, tetramers, octamers, and dodecamers generated by one or more rounds of ligation) were then cloned back into XhoI-SalI digested pSP73 and transformed into the STBL2™ competent cells (Life Technologies, Gaithersburg, Md.). Both orientations of the insert were recovered in some cases. Next, the dodecamer and some shorter polymers were moved to sites downstream of different promoters in different plasmids. For example, they are cloned into the XhoI site of the pUAST vector (Brand and Perrimon, "Targeted Gene Expression as a Means of Altering Cell Fates and Generating Dominant Phenotypes," Development 118:401–415 (1993), which is herbey incorporated by reference) and used in the Drosophila germ line transformation. A list of engineered BBS genes is listed in FIG. 7.

Example 6

In vitro Large Scale Production of Pentavalent RNA Aptamer And Its Binding to Drosophila B52

Figure 10A:
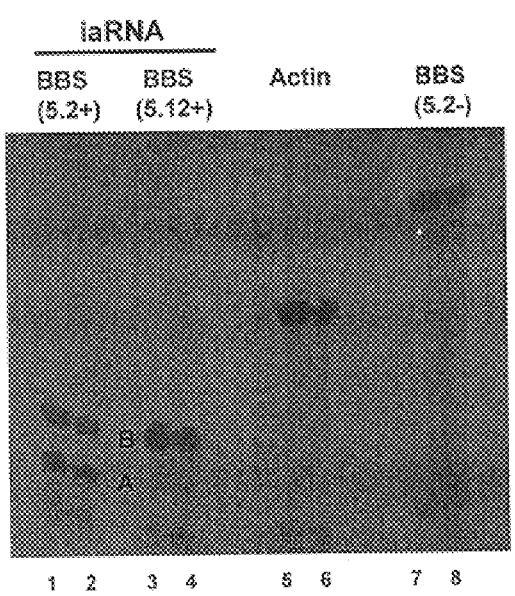
FIGS. 10A and 10B are images which illustrate the effectiveness of large scale production of the mature pentavalent RNA and its binding to B52.
Figure 10B:
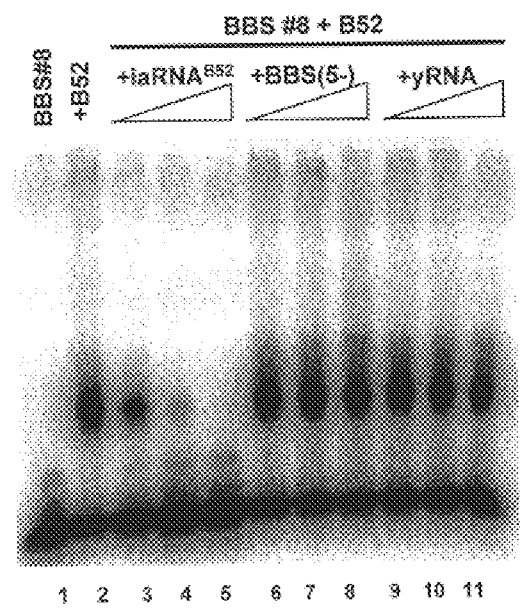

The pentavalent RNA aptamer can be transcribed and self-cleaved in vitro in large scale. The pentavalent RNA aptamer transcribed from two different templates was compared after being run on a polyacrylamide preparative gel and visualized by UV shadowing as shown in FIG. 10A. A 1:1 ratio of Fragment A to Fragment B was observed for the pentavalent RNA aptamer transcribed from the BBS (5.2) templates (Lanes 1 and 2, FIG. 10A), and a roughly 1:10 ratio was observed for the pentavalent RNA aptamer transcribed from the BBS (5.12) templates (Lanes 3 and 4, FIG. 10A). No other bands representing higher molecular weight transcripts were visible in these lanes. The self-cleavage reaction was virtually completed during the overnight transcription. The activity of the gel purified Fragment B—about 100 μg was recovered from gel purification—was tested in a competition binding assay (FIG. 10B). BBS #8, the strongest-binding monovalent RNA aptamer, was used as the probe in a gel shift assay with gel purified pentavalent RNA aptamer and its antisense RNA, BBS(5–), as competitors. The same amount of purified Torulla yeast RNA (Ambion) consisting of fragments of 300–500 bases (yRNA) was used as a control. The pentavalent RNA aptamer competed more efficiently than monovalent aptamers for binding to B52.

Example 7

Increased Avidity of the Pentavalent RNA Aptamer for B52

As shown in FIG. 3A, the ribozyme cleavage of a single unit of the immature RNA transcript BBS(5.1) yielded equal molar amount of Fragment A and C. Fragment C, which contains no binding site, served as an internal loading control in a band shift assay to assess the avidity of the pentavalent construct. During the transcription reaction, the extent of self-cleavage reached about 90% (FIG. 3A, Lane 1). All BBS sequences used in constructing the pentavalent RNA aptamer had been previously tested individually for their ability to bind B52, exhibiting an average dissociation constant of 50 nM (ranging from 20 to 80 nM). The multivalent RNA aptamers bound B52 10-fold more avidly than the individual monovalent RNA aptamers, as shown here compared to the strong-binding primary aptamer BBS #14 (Lanes 2–4 vs. Lanes 6–8, FIG. 9A). Dimeric, tetrameric, octameric, and dodecameric pentavalent RNA aptamer templates yielded RNA Fragments A, B, and C, with the molar fraction of Fragment B (the functional pentavalent RNA aptamer) increasing in proportion to the length of the template. Indeed, all four constructs showed almost identical pattern of bands on a native gel (FIG. 9B, Lanes 4, 7, 10, and 13), with a notable increase in the ratio of Fragment B to C as the length of the template increase. The pentavalent RNA aptamers produced by each construct showed identical affinities for B52. The similarity of the pattern of bands produced by transcriptional templates of different length also indicated that each ribozyme folded correctly and acted independently.

Example 8
Inhibiting B52 Function With the Pentavalent RNA Aptamer

Figure 11A:
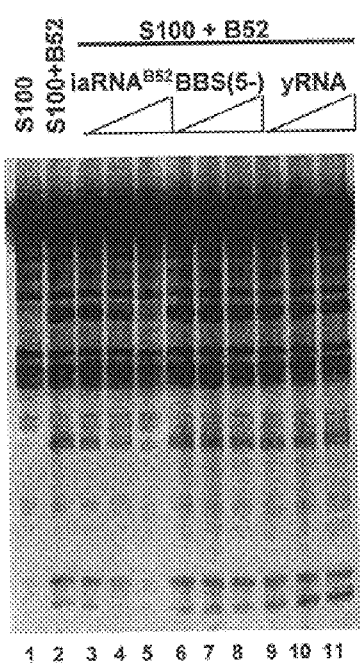
FIGS. 11A and 11B are images which illustrate the ability of the mature pentavalent RNA aptamer to modify B52 function in vitro.

The pentavalent RNA aptamer was produced in vitro in large scale and tested for its ability to alter B52 function. Recombinant B52 complements a Drosophila S100 splicing deficient extract, allowing the accurate splicing of aftz pre-mRNA derivative. Gel purified pentavalent RNA aptamer (Fragment B) inhibited the generation of spliced product as well as several splicing intermediates (FIG. 11A, Lanes 3–5), while the same amount of the antisense BBS (5.1) RNA or yeast genomic RNA of comparable size caused no change in splicing activity in this assay (FIG. 11A, Lanes 6–8 and 9–11). The lack of accumulation of splicing intermediates in the BBS-inhibited splicing reactions indicates that B52, like some other SR proteins, acts at an early step in splicing (Fu, "The Superfamily of Arginine/Serine-Rich Splicing Factors," *RNA* 1:663–680 (1995); Manley and Tacke, "SR Proteins and Splicing Control," *Genes Dev.* 10(3):1569–1579 (1996), both of which are hereby incorporated by reference). To confirm the specificity of this inhibition, the splicing activity suppressed by the pentavalent RNA aptamer was restored by adding additional amounts of B52 to the suppressed assay mixture. These results support the theory that the inhibition is through the pentavalent RNA aptamer binding to the RRMs of B52, which prevents interaction of B52 with theftz pre-mRNA.

Example 9
Increasing B52 Activity With the Pentavalent RNA Aptamer

Figure 11B:
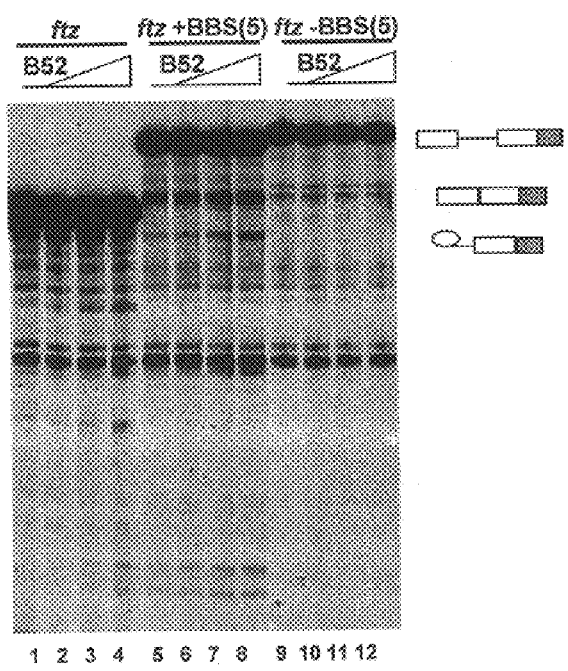

While B52 can be neutralized or sequestered by the addition of pentavalent RNA aptamer in trans in a fashion similar to antibody depletion of a protein as shown in Example 8, appending the pentavalent RNA aptamer sequence directly to pre-mRNA has the opposite effect. Selected aptamer RNAs that bind to other SR proteins have been shown to function as synthetic splicing enhancers when multiple copies are inserted in pre-mRNA substrates (Tacke and Manley, "The Human Splicing Factors ASF/SF2 and SC35 Possess Distinct, Functionally Significant RNA Binding Specificities," *EMBO J.* 14:3540–3551 (1995); Tacke et al., "Sequence-Specific RNA Binding by an SR Protein Requires RS Domain Phosphorylation: Creation of an SRp4 O-Specific Splicing Enhancer," *Proc. Natl. Acad. Sci. USA* 94:1148–1153 (1997), both of which are hereby incorporated by reference). A splicing substrate containing the BBS pentamer affixed to the 3' end of the fz pre-mRNA was constructed and used in the splicing assay described in Example 8. An enhancement in splicing activity was observed (FIG. 11B). Notably, the S100 preparation has trace amount of B52, not sufficient to prompt splicing of the original ftz substrate, but enough to activate the splicing of the substrate bearing BBSs in the 3' exon (FIG. 11B, Lane 5 vs. 1). The strong affinity of B52 to the pentavalent RNA aptamer presumably allows B52 in low concentration o bind this BBS-modified pre-mRNA and activate splicing.

Example 10
Accumulation and Half-life of the Pentavalent RNA Aptamer in Cells

To evaluate the expression of the pentavalent RNA aptamer in vivo, BS-expressing genes were introduced into cultured Drosophila S2 cells to assess the bundance and half-life of the pentavalent RNA aptamer. Transient expression of the pentavalent RNA aptamer was measured by quantitative RNase protection assay with in vitro transcribed pentavalent RNA aptamer as standards. Two strongly inducible promoters, a metallothionein promoter and a heat shock promoter, were used to drive BBS transcriptional templates of different length. While a metallothionein promoter (in the MtnBBS constructs) can be induced by $Cu^{2+}$ in a few hours, a heat shock promoter (in the HicBBS constructs) becomes fully active within minutes. The rapid induction of the heat shock promoter also allows a more precise measurement of the half-life of the pentavalent RNA aptamer. As shown in FIG. 12A, both promoters resulted in similar levels of RNA accumulation when an identical template was transcribed. After measuring the transfection efficiency and by comparing the pentavalent RNA aptamer in the total RNA sample to in vitro transcribed pentavalent RNA aptamer standards, it was estimated that pentavalent RNA aptamer transcribed from a dodecameric template can accumulate to a level equivalent to 0.1% of total RNA or 10% of total mRNA. This abundant accumulation of pentavalent RNA aptamer was also confirmed using another Drosophila cell line, Kc.

To measure the half-life of the pentavalent RNA aptamer, the cells were treated with actinomycin D (Lindquist, "Varying Patterns of Protein Synthesis in Drosophila During Heat Shock: Implications for Regulation," *Dev. Biol.* 77:463–479 (1980), which is hereby incorporated by reference) to stop all transcription immediately after heat shock, and the level of the pentavalent RNA aptamer in cells harvested at 0, 2, 4, 8 hours thereafter was assayed. As shown in FIG. 12A, the half-life of the pentavalent RNA aptamer was about four hours (Lanes 2–5 and 7–10).

Example 11
Temporally and Spatially Regulated Expression of the Pentavalent RNA Aptamer in Drosophila To express the pentavalent RNA aptamer in flies, two systems were compared. First, a heat shock promoter was used to directly control the expression of the pentavalent RNA aptamer in the HicBBS strains. Because of the precise temporal control over gene expression, the HicBBS(5.12) strain (FIG. 12 B, Lanes 9 and 10) was used in cytological experiments. Since B52 is a nuclear protein, the pentavalent RNA aptamer was designed to be retained inside the nuclei. When the BBS transcriptional template is cloned into a standard in vivo expression vector having a downstream poly-adenylation signal, the ribozyme-cleaved pentavalent RNA aptamer does not bear a poly-A tail and, therefore, should remain nuclear. The exclusiveness of nuclear retention of the accumulated pentavalent RNA aptamer was demonstrated by in situ hybridization with whole mount salivary gland tissue as shown in FIG. 13A. The co-compartmentalization of pentavalent RNA aptamer with its target not only facilitated their encounter with each other, but also achieved a considerable subcellular concentration of the pentavalent RNA aptamer. In Drosophila, the polytene chromosomes provided an ideal venue to visualize the in vivo interaction between B52 and BBS, since the distribution of B52 protein on the polytene chromosomes had been well-characterized (Champlin et al., "Characterization of a Drosophila Protein Associated With Boundaries of Transcriptionally Active Chromatin," *Genes Dev.* 5:1611–1621 (1991); Champlin and Lis, "Distribution of B52 Within a Chromosomal Locus Depends on the Level of Transcription," *Molec. Biol. Cell.* 5:71–79 (1994), which are hereby incorporated by reference). The locus of transgene insertion was mapped (FIG. 13B, left panel) by polytene in situ hybridization. With a similar technique, expression of the pentavalent RNA aptamer was visualized as a medium-sized puff (FIG. 13B, middle panel). Immunofluorescence with an anti-B52 antibody showed massive recruitment of B52 upon heat shock to the insertion site of the HicBBS (5.12) transgene (FIG. 13B, right panel). This co-localization of B52 and its pentavalent RNA aptamer indicate an interaction between them in vivo. Notably, this B52 recruitment to the site of nascent pentavalent RNA aptamer synthesis far exceeded that at the native heat shock loci, which are normally the strongest sites labeled during heat shock. Also, at the transgenic insertion site, B52 covers the entire puff where RNA is made, in contrast to the puff bracketing pattern seen at the native heat shock loci.

To further enhance the accumulation of pentavalent RNA aptamer and to achieve spatial control of expression in different tissues, BBS transgenes activated by the yeast transcription factor GAL4 (Brand and Perrimon, "Targeted Gene Expression as a Means of Altering Cell Fates and Generating Dominant Phenotypes," *Development* 118:401–415 (1993), which is hereby incorporated by reference) were constructed. When GAL4 expression was controlled by a heat shock promoter (in the hsGAL4 construct), an additional step of amplification in the pentavalent RNA aptamer expression was achieved, as shown in FIG. 12B. When identical templates (in this case dodecameric ones) were used, indirect heat shock induction via the GAL4-UAS system resulted in a several fold increase in pentavalent RNA aptamer accumulation (FIG. 12B, Lanes 8 vs. 10). Even without heat shock, the basal level transcription from the heat shock promoter provided sufficient GAL4 to sustain a steady-state pentavalent RNA aptamer level in the heterozygous hsGAL4-UASBBS(5.12) flies comparable to that in the homozygous HicBBS(5.12) flies immediately following heat treatment (FIG. 12B, Lanes 7 vs. 10).

Example 12
Efficacy of the Pentavalent RNA Aptamer as B52 Antagonist at the Organismic Level Previous genetic studies had shown that the level of B52 is critical to Drosophila development. While a B52 deletion resulted in lethality (Ring and Lis, "The SR Protein B52/SRp55 is Essential for Drosophila Development," *Mol. Cell. Biol.* 14:7499–7506 (1994), which is hereby incorporated by reference), overproduction of B52 also caused lethality or morphological defects (Kraus and Lis, "The Concentration of B52, an Essential Splicing Factor and Regulator of Splice Site Choice, is Critical for Drosophila Development," *Mol. Cell. Biol.* 14:5360–5370 (1994), which is hereby incorporated by reference). To appraise the in vivo efficacy of the pentavalent RNA aptamer as an inhibitor of B52, the phenotype caused by high level expression of the pentavalent RNA aptamer was examined. It was first noticed that the homozygous double transgenic line hsGAL4-UASBBS (5.12) produces many fewer progeny than wild-type strains, while the homozygous hsGAL4 line is as viable as wild-type. To confirm that the reduced viability is caused by BBS expression and to estimate the maximum tolerated dose, a genetic test was designed in which flies carrying different copy numbers of either transgene can be identified and counted (FIG. 14 & 15). Two pairs of isogenetic double transgenic flies were synthesized such that each pair has an hsGAL4-UASBBS line and an UASBBS-UASBBS line. The only difference between the two lines is the chromosome carrying hsGAL4 in one line is replaced by a chromosome carrying an UASBBS in the other. By self-crossing the double balanced stocks of both lines, the effect of the active transgenes in one line with that of the dormant transgenes in the other could be compared. FIG. 15B shows the results of the two experiments. Reduced viability was observed when more than one copy of UASBBS(5.12) was present. The overall morphology of the surviving animals appeared normal.

Figure 16:
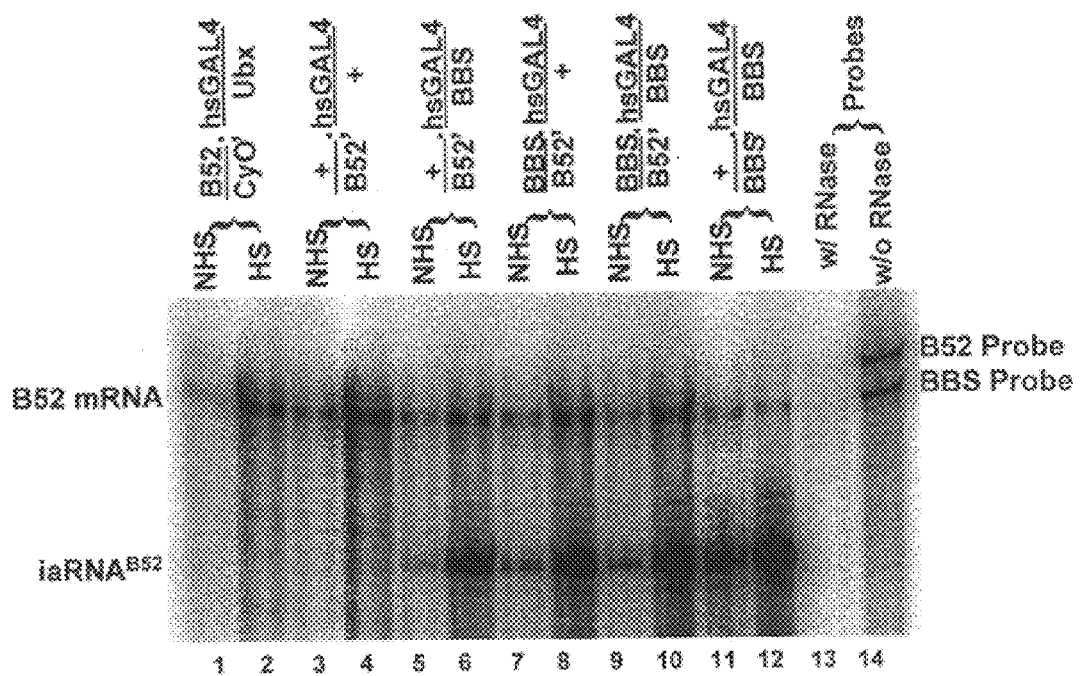
FIG. 16 is an image of a RNase protection assay which confirms GAL4 driven expression of BBS and over expression of B52 in the heterozygous triple transgenic flies. An RNA probe derived from the sequence coding for the RRMs was used to detect B52 mRNA, and a probe covering part of the monomeric unit of the mature pentavalent RNA aptamer was used to detect BBS. HsGAL4 driven expression of B52 and/or BBS, and the response of transcription to heat treatment in animals produced by different crosses are shown. Genotypes of the heterozygous flies are indicated. 12 $\mu$g total RNA was used in the assay for B52 MRNA, while 1 $\mu$g total RNA was used for detecting BBS. The samples from same flies were then pooled and run in the same lane.

A more rigorous verification of the pentavalent RNA aptamer's mechanism of action and an assessment of its efficacy was conducted in flies that over produce B52, which had been sensitized to the change of B52 level. This was performed under the assumption that co-expression of the pentavalent RNA aptamer may suppress the phenotypes caused by B52 overexpression if it indeed acts as a B52 antagonist. To test this theory, transgenic fly lines were produced containing genes that can over-express both B52 (UASB52) and pentavalent RNA aptamer (UASBBS). Both genes have a promoter that is strongly activated by the GAL4 activator of yeast that has been also introduced to transgenic fly lines (FIG. 14). The GAL4 gene itself can be controlled by a heat shock promoter or various developmental enhancers. The expression of both B52 and BBS in the heterozygous triple transgenic flies were examined by RNase protection assay (FIG. 16). The expression of the GAL4 gene was also confirmed by mating the GAL4 lines with a UASLacZ strain followed by a β-gal assay on whole mount larvae tissues.

Crosses that place the GAL4 gene and the UASB52 gene in the same strain can produce five different phenotypes depending on the pattern and level of GAL4 expression (Kraus and Lis, "The Concentration of B52, an Essential Splicing Factor and Regulator of Splice Site Choice, is Critical for Drosophila Development," *Mol. Cell. Biol.* 14:5360–5370 (1994), which is hereby incorporated by reference, and FIG. 17H). Remarkably, the introduction of a UASBBS gene into a strain that has this B52 over production rescued all of these phenotypes. One dramatic phenotype of B52 over-expression is the absence of larval salivary glands. This salivary gland development is largely restored by the co-expression of pentavalent RNA aptamer (compare FIGS. 17B–17D). In addition, bristles of the adult notum are missing in a line that over-expresses an UASB52 gene. Here too, the bristles are largely restored to their normal number by co-expression of the pentavalent RNA aptamer (compare FIGS. 17E–17G). Abnormal phenotypes of wings and abdominal sternites, as well as the lethality caused by B52 over-expression were also all suppressed in the presence of the pentavalent RNA aptamer (FIG. 17H). Detailed description of the phenotypes is provided below. Also examined was the effect of pentavalent RNA aptamer dosage in rescuing lethality and bristle development quantitatively using the cross scheme of FIG. 17I, where the dose of pentavalent RNA aptamer was varied by expressing pentavalent RNA aptamer genes containing different numbers (i.e., dimers, tetramers, octamers, or dodecamers) of pentavalent RNA aptamer units. The degree of rescue of both B52 over-expression phenotypes was proportional to pentavalent RNA aptamer dose. FIGS. 17J and 17K depict the dosage-dependent effect of the pentavalent RNA aptamer on bristle development and viability, respectively. These results demonstrate that pentavalent RNA aptamer reverses all of the phenotypes caused by B52 over-expression and strongly supports the hypothesis that the pentavalent RNA aptamer can inhibit B52 function in vivo. Four different kinds of morphological changes and lethality were observed with different level and temporal/spatial pattern of B52 overexpression. Larval phenotypes were examined on the 6th day after mating; surviving adults on the 16th day were examined and counted (male and female separately). The following is a qualitative and, where possible, quantitative description of the phenotypes caused by B52 overexpression and its suppression by co-expressing the pentavalent RNA aptamer. When both the additional B52 gene and the BBS (iaRNA) gene are active the fly is designated as {B52+BBS}. The patterns of GAL4 expression was described in Kraus and Lis ("The Concentration of B52, an Essential Splicing Factor and Regulator of Splice Site Choice, is Critical for Drosophila Development," *Mol. Cell. Biol.* 14:5360–5370 (1994), which is hereby incorporated by reference).

Salvary Glands

GAL4 source: hsGAL4, dppGAL4, G-17.

Phenotype: Glands are extremely small or absent altogether.

Suppression: Glands bigger than 1/2 of its normal size were counted as averted phenotype. Size variation and morphological features were recorded. When dppGAL4 was used as the GAL4 source, a 100% suppression was observed in {B52+BBS}. However, the glands in the third instar larvae appeared to be less translucent, less smooth, and the size of both individual cells and the whole glands appeared to be more variable.

Bristles

GAL4 source: hsGAL4

Phenotype: Long bristles or macrochaetes on the thorax, head and legs are shorter, thinner, or absent altogether.

Suppression: Seven pairs of bristles were chosen to score: the posterior super-alar, the dorso-centrals, the post-alars, and the scutellars. Each full length bristle was counted as 1. The wild type flies have the score 14. The sum of length of this set of bristles in the transgenic flies were estimated and given a score less or equal to 14. 20 animals were scored for each cross. The suppression of this phenotype showed a dosage response to BBS.

Abdominal sternites

GAL4 source: G-17, and I-65

Phenotype: Chaetes, especially on 3s, 4s, and 5s, are missing or misplaced. The abnormal stemite usually still have more than 10 chaetes. The defects are usually manifest in 40% adults of both sex.

Suppression: Any missing or misplacement was counted as a defect. When G-17 was used as the GAL4 source, almost all defects were obviated in {B52+BBS}. When 1–65 was used, about 40% viable adults of {B52+BBS} showed this defect.

Wings

GAL4 source: dppGAL4, and hsGAL4.

Phenotype: The most severe phenotype is seen with dppGal4 (100%), where the wings are folded as they are within the pupal case. The less severe phenotype is seen with hsGal4 (30–70%), where the wings may be curled or wrinkled at the ends.

Suppression: The severity of the phenotype was ordered as follows: folded>curled>wrinkled>easily ripped>normal. Folded, curled, and wrinkled were counted. When dppGAL4 was used as the GAL4 source, about 20% unfolded in {B52+BBS}. When hsGAL4 was used, 5% remained curled in {B52+BBS}.

Lethality

GAL4 source: hsGAL4, dppGAL4, A-25, I-65, G-17.

Phenotype: Lethality can occur at different stages of development. A-25: 100% third instar lethal. I-65: 100% first instar lethal.

Suppression: Reduced viability was revealed by comparing the number of adult living progeny from the experimental cross to that of control crosses. When total lethality occurs, the developmental stage was recorded. Survival beyond this stage was counted as suppression. Surviving adults in each cross were counted. Morphological features of the surviving animal were recorded. In all cases viability was restored to different degrees. When A-25 was used, the surviving adults of {B52+BBS} had wing defects. When I-65 was used, the survived adults {B52+BBS} had abdominal sternite defects.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A monovalent RNA aptamer that binds to Drosophila splicing factor B52.

2. A multivalent RNA aptamer comprising:
   at least two RNA aptamer sequences linked together, each of the at least two RNA aptamer sequences being capable of binding a target molecule; and
   an exonuclease-blocking sequence linked to one of the at least two RNA aptamer sequences.

3. A constructed DNA molecule comprising:
   a plurality of monomeric DNA sequences linked together to form a single DNA chain, each monomeric DNA sequence encoding a multivalent RNA aptamer comprising at least two RNA aptamer sequences linked together, each of the at least two RNA aptamer sequences being capable of binding a target molecule.

4. The monovalent RNA aptamer of claim 1, wherein the RNA aptamer has a nucleotide sequence corresponding to SEQ. ID. No. 1, SEQ. ID. No. 2, SEQ. ID. No. 3, SEQ. ID. No. 4, or SEQ. ID. No. 5.

5. A constructed DNA molecule encoding a monovalent RNA aptamer of claim 1.

6. The constructed DNA molecule of claim 5, wherein the DNA molecule has a nucleotide sequence corresponding to SEQ. ID. No. 9, SEQ. ID. No. 10, SEQ. ID. No. 11, or SEQ. ID. No. 12.

7. An expression system comprising an expression vector into which is inserted a heterologous DNA molecule of claim 5.

8. The expression system of claim 7, wherein the heterologous DNA molecule is inserted into the vector in proper orientation.

9. A host cell containing a heterologous DNA molecule of claim 5.

10. The multivalent RNA aptamer of claim 2, wherein five RNA aptamer sequences are linked together.

11. The multivalent RNA aptamer of claim 2, wherein the at least two RNA aptamer sequences each bind to a splicing factor.

12. The multivalent RNA aptamer of claim 11, wherein the splicing factor is Drosophila splicing factor B52.

13. The multivalent RNA aptamer of claim 12, wherein the at least two RNA aptamer sequences each have a nucleotide sequence comprising SEQ. ID. No. 5.

14. The multivalent RNA aptamer of claim 2, further comprising:
   an exonuclease-blocking sequence linked to one of the at least two RNA aptamer sequences.

15. The multivalent RNA aptamer of claim 2, wherein the exonuclease-blocking sequence comprises:
   a UUCG tetra-loop element and
   a S35 motif formed by the 5' and 3' ends of the multivalent RNA aptamer.

16. The multivalent RNA aptamer of claim 2, wherein each of the at least two RNA aptamer sequences comprise:
   a hairpin loop structure having a neck portion characterized by a high degree of base-pairing and a loop portion characterized by non-paired bases.

17. The multivalent RNA aptamer of claim 16, wherein each of the at least two RNA aptamer sequences further comprise:
   a target-binding sequence which forms part of the neck portion and the entire loop portion.

18. A constructed DNA molecule encoding a multivalent RNA aptamer of claim 2.

19. The constructed DNA molecule of claim 18, wherein the constructed DNA molecule has a nucleotide sequence corresponding to SEQ. ID. No. 13.

20. The constructed DNA molecule of claim 18, wherein the constructed DNA molecule comprises a plurality of monomeric DNA sequences linked together in a single DNA chain, each of the plurality of monomeric DNA sequences encoding a multivalent RNA aptamer.

21. The constructed DNA molecule of claim 20, wherein each of the plurality of monomeric DNA sequences is substantially identical.

22. The constructed DNA molecule of claim 21, wherein each of the plurality of monomeric DNA sequences has a nucleotide sequence corresponding to SEQ. ID. No. 13.

23. The constructed DNA molecule of claim 20, wherein each of the plurality of monomeric DNA sequences also encodes a cis-acting ribozyme.

24. The constructed DNA molecule of claim 22, wherein the cis-acting ribozyme is a hammerhead-type ribozyme.

25. The constructed DNA molecule of claim 18, wherein the multivalent RNA aptamer comprises five RNA aptamer sequences linked together.

26. An expression system comprising an expression vector into which is inserted a heterologous DNA molecule of claim 18.

27. The expression system of claim 26, wherein the heterologous DNA molecule is inserted into the vector in proper orientation.

28. A host cell containing a heterologous DNA molecule of claim 18.

29. The host cell of claim 28, wherein the host cell is present in a cell culture.

30. A method of expressing a multivalent RNA aptamer in a cell comprising:
introducing a DNA molecule of claim 18 into a cell under conditions effective to express the multivalent RNA aptamer.

31. An engineered gene encoding a multivalent RNA aptamer comprising:
a DNA sequence encoding a multivalent RNA aptamer of claim 2 and
a regulatory sequence which controls expression of the DNA sequence encoding a multivalent RNA aptamer.

32. The gene of claim 31, wherein the regulatory sequence is a promoter.

33. The gene of claim 32, wherein the promoter is selected from the group consisting of a T7 promoter, a hsp70 promoter, a Mtn promoter, a UAShs promoter, and functional fragments thereof.

34. The gene of claim 31, wherein the DNA sequence has a nucleotide sequence corresponding to SEQ. ID. No. 13.

35. The gene of claim 31, wherein the DNA sequence comprises:
a plurality of monomeric DNA sequences each encoding a multivalent RNA aptamer.

36. The gene of claim 35, wherein each of the plurality of monomeric DNA sequences is substantially identical.

37. The gene of claim 36, wherein each of the plurality of monomeric DNA sequences has a nucleotide sequence corresponding to SEQ. ID. No. 13.

38. The gene of claim 35, wherein each of the plurality of monomeric sequences also encodes a cis-acting ribozyme.

39. The gene of claim 38, wherein the cis-acting ribozyme is a hammerhead-type ribozyme.

40. The gene of claim 31, wherein the multivalent RNA aptamer comprises five RNA aptamer sequences linked together.

41. The gene of claim 40, wherein each of the five RNA aptamer sequences comprises a B52-binding sequence.

42. An expression system comprising an expression vector into which is inserted a heterologous gene of claim 31.

43. The expression system according to claim 42, wherein the heterologous gene is inserted into the vector in proper orientation.

44. A host cell containing a heterologous gene of claim 31.

45. The host cell of claim 44, wherein the host cell is present in a cell culture.

46. A method of expressing a multivalent RNA aptamer in a cell comprising:
introducing an engineered gene of claim 31 into a cell under conditions effective to express the multivalent RNA aptamer.

47. The method of claim 46, wherein the promoter is an inducible promoter and the effective conditions are conditions which induce the inducible promoter.

48. The constructed DNA molecule of claim 3, wherein each of the plurality of monomeric DNA sequences is substantially identical.

49. The constructed DNA molecule of claim 3, wherein each of the plurality of monomeric DNA sequences also encodes a cis-acting ribozyme.

50. The constructed DNA molecule of claim 49, wherein the cis-acting ribozyme is a hammerhead-type ribozyme.

51. An expression system comprising an expression vector into which is inserted a heterologous DNA molecule of claim 2.

52. The expression system of claim 51, wherein the heterologous DNA molecule is inserted into the vector in proper orientation.

53. A host cell containing a heterologous DNA molecule of claim 2.

54. The host cell of claim 53, wherein the host cell is present in a cell culture.

55. An engineered gene comprising:
the constructed DNA molecule of claim 2 and
a regulatory sequence which controls expression of each monomeric DNA sequence encoding a multivalent RNA aptamer.

56. The gene of claim 55, wherein the regulatory sequence is a promoter.

57. The gene of claim 55, wherein each of the plurality of monomeric DNA sequences is substantially identical.

58. The gene of claim 55, wherein each of the plurality of monomeric sequences also encodes a cis-acting ribozyme.

59. The gene of claim 58, wherein the cis-acting ribozyme is a hammerhead-type ribozyme.

60. An expression system comprising an expression vector into which is inserted a heterologous gene of claim 55.

61. A host cell containing a heterologous gene of claim 55.

62. The host cell of claim 28, wherein the host cell is present in a cell culture.

* * * * *

UNITED STATES PATENT AND TRADEMARK OFFICE
CERTIFICATE OF CORRECTION

PATENT NO.    : 6,458,559 B1                                           Page 1 of 1
DATED         : October 1, 2002
INVENTOR(S)   : Shi et al.

It is certified that error appears in the above-identified patent and that said Letters Patent is hereby corrected as shown below:

Column 1,
Line 9, "U.S. Public Health Service" should be deleted and in its place -- the National Institutes of Health -- should be inserted.

Column 54,
Lines 41 and 42, Claim 14 should be deleted in its entirety.

Column 55,
Line 12, delete "22" and insert -- 23 -- in its place.

Column 56,
Line 32, 37, and 41, delete "2" and insert -- 3 -- in its place.
Line 56, delete "28" and insert -- 61 -- in its place.

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,458,559 B1
APPLICATION NO. : 09/296328
DATED : October 1, 2002
INVENTOR(S) : Shi et al.

It is certified that error appears in the above-identified patent and that said Letters Patent is hereby corrected as shown below:

Col. 1 at lines 8-11, delete "This invention was made in part with Government support under U.S. Public Health Service Grant GM40918 and U.S.D.A. Hatch Project Grant NY(c)-181413. The Government may have certain rights to this invention." and insert --This invention was made with government support under grant GM40918 awarded by U.S. Public Health Service and grant NY(c)-181413 awarded by U.S.D.A. Hatch Project. The government has certain rights in the invention-- in its place.

Signed and Sealed this

Fourteenth Day of April, 2009

JOHN DOLL
*Acting Director of the United States Patent and Trademark Office*